(12) United States Patent
Harrison et al.

(10) Patent No.: US 7,781,577 B2
(45) Date of Patent: Aug. 24, 2010

(54) INHIBITORS OF SODIUM GLUCOSE CO-TRANSPORTER 2 AND METHODS OF THEIR USE

(75) Inventors: Bryce Alden Harrison, Hamilton, NJ (US); Spencer David Kimball, East Windsor, NJ (US); Ross Mabon, Princeton, NJ (US); David Brent Rawlins, Morrisville, PA (US); Nicole C Goodwin, Pennington, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 220 days.

(21) Appl. No.: 11/862,690

(22) Filed: Sep. 27, 2007

(65) Prior Publication Data

US 2008/0113922 A1  May 15, 2008

Related U.S. Application Data

(60) Provisional application No. 60/848,156, filed on Sep. 29, 2006, provisional application No. 60/905,714, filed on Mar. 8, 2007, provisional application No. 60/948,780, filed on Jul. 10, 2007.

(51) Int. Cl.
| | |
|---|---|
| A61K 31/7008 | (2006.01) |
| A61K 31/7034 | (2006.01) |
| A61K 31/7042 | (2006.01) |
| C07H 5/06 | (2006.01) |
| C07H 5/10 | (2006.01) |
| C07H 7/04 | (2006.01) |
| C07H 7/06 | (2006.01) |

(52) U.S. Cl. .................... 536/29.1; 514/23; 514/34; 514/25; 514/42; 536/53
(58) Field of Classification Search .............. None
See application file for complete search history.

(56) References Cited

U.S. PATENT DOCUMENTS

| | | | |
|---|---|---|---|
| 6,414,126 | B1 | 7/2002 | Ellsworth |
| 6,515,117 | B2 | 2/2003 | Ellsworth |
| 6,555,519 | B2 | 4/2003 | Washburn |
| 6,562,791 | B1 | 5/2003 | Maurya |
| 6,683,056 | B2 | 1/2004 | Washburn |
| 6,774,112 | B2 | 8/2004 | Gougoutas |
| 6,927,294 | B1 * | 8/2005 | Petasis et al. ............... 546/183 |
| 6,936,590 | B2 | 8/2005 | Washburn |
| 7,045,665 | B2 | 5/2006 | Fujikura |
| 7,053,060 | B2 | 5/2006 | Fujikura |
| 7,202,350 | B2 | 4/2007 | Imamura |
| 7,250,522 | B2 * | 7/2007 | Sato et al. ............... 549/28 |
| 2002/0068705 | A1 | 6/2002 | Ruediger |
| 2003/0087843 | A1 | 5/2003 | Washburn |
| 2003/0181402 | A1 | 9/2003 | Wei |
| 2004/0059105 | A1 | 3/2004 | Sabesan |
| 2004/0077672 | A1 | 4/2004 | Prudhomme |
| 2004/0138439 | A1 | 7/2004 | Deshpande |
| 2004/0152721 | A1 | 8/2004 | Prudhomme |
| 2004/0242508 | A1 | 12/2004 | Prudhomme |
| 2004/0248892 | A1 | 12/2004 | Wang |
| 2004/0259819 | A1 | 12/2004 | Frick |
| 2004/0259876 | A1 | 12/2004 | Shiraishi |
| 2005/0014704 | A1 | 1/2005 | Frick |
| 2005/0187168 | A1 | 8/2005 | Eickelmann |
| 2005/0209166 | A1 | 9/2005 | Eckhardt |
| 2005/0209176 | A1 | 9/2005 | Meutermans |
| 2005/0233982 | A1 | 10/2005 | Himmelsbach |
| 2005/0256317 | A1 * | 11/2005 | Sato et al. ............... 549/28 |
| 2006/0009400 | A1 | 1/2006 | Eckhardt |
| 2006/0019948 | A1 | 1/2006 | Eckhardt |
| 2006/0025349 | A1 | 2/2006 | Eckhardt |
| 2006/0025352 | A1 | 2/2006 | Fujikura |
| 2006/0035840 | A1 | 2/2006 | Fujikura |
| 2006/0035841 | A1 | 2/2006 | Eckhardt |
| 2006/0035844 | A1 | 2/2006 | Ito |
| 2006/0035847 | A1 | 2/2006 | Fujikura |
| 2006/0074031 | A1 | 4/2006 | Eckhardt |
| 2006/0189548 | A1 | 8/2006 | Himmelsbach |
| 2006/0194809 | A1 | 8/2006 | Kakinuma |
| 2006/0217427 | A1 | 9/2006 | Lampe |
| 2006/0240496 | A1 | 10/2006 | Anne |
| 2007/0049537 | A1 | 3/2007 | Eckhardt |
| 2007/0060545 | A1 | 3/2007 | Nomura |
| 2007/0161787 | A1 | 7/2007 | Imamura |
| 2007/0197449 | A1 | 8/2007 | Fushimi |
| 2007/0270452 | A1 | 11/2007 | Blagg |

(Continued)

FOREIGN PATENT DOCUMENTS

DE    10 2004 039 096    2/2006

(Continued)

OTHER PUBLICATIONS

Merriam-Webster's Collegiate Dictionary, Tenth Edition, published 1998 by Merriam-Webster, incorporated, pp. 924 and 935.*
The Merck Manual of Diagnosis and Therapy, Seventeenth Edition, published 1999 by Merck Research Laboratories, pp. 165-168 and 1654-1657.*
Bozó et al., "An economic synthesis of 1,2,3,4-tetra-O-acetyl-5-thio-d-xylopyranose and its transformation into 4-substituted-phenyl 1,5-dithio-d-xylopyranosides possessing antithrombotic activity" Carbohydrate Research (1998) vol. 308 pp. 297-310.*
Bose, A. K. et al., *Tetrahedron* 56(31):5603-5619 (2000).
Dudash et al., *Bioorg Med Chem Lett* 14:5121-5125 (2004).
Ehrenkranz et al., *Diabetes Metab Res Rev* 21:31-38 (2005).

(Continued)

*Primary Examiner*—Eric S Olson
(74) *Attorney, Agent, or Firm*—Max Bachrach

(57) ABSTRACT

Compounds and pharmaceutical compositions comprising them are disclosed that may be useful for the treatment of diseases and disorders such as diabetes and obesity.

27 Claims, 1 Drawing Sheet

U.S. PATENT DOCUMENTS

Figure 1:
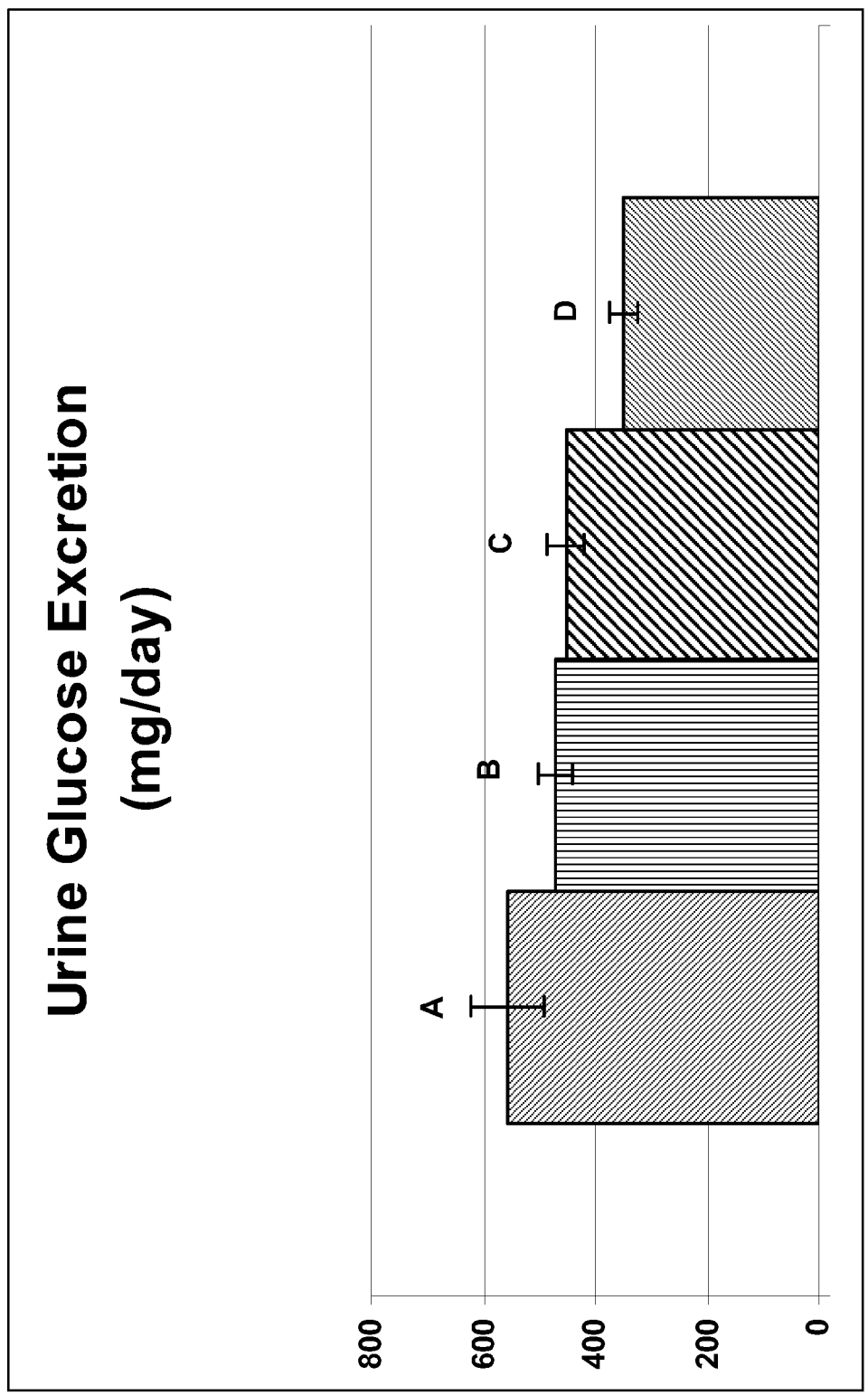

| | | |
|---|---|---|
| 2007/0293690 A1 | 12/2007 | Tomiyama |
| 2008/0021066 A1 | 1/2008 | Condon |
| 2008/0045466 A1 | 2/2008 | Katsuno |
| 2008/0132563 A1 | 6/2008 | Kakinuma |
| 2008/0221164 A1 | 9/2008 | Goodwin et al. |
| 2009/0030198 A1 | 1/2009 | Goodwin |
| 2010/0016422 A1 | 1/2010 | De Paul |

FOREIGN PATENT DOCUMENTS

| | | |
|---|---|---|
| DE | 10 2004 046 583 | 3/2006 |
| JP | 100204004 | 8/1998 |
| WO | WO 9516049 | 6/1995 |
| WO | WO 03011880 | 2/2003 |
| WO | WO 03080553 | 10/2003 |
| WO | WO 03099836 | 12/2003 |
| WO | WO 2004035582 | 4/2004 |
| WO | WO 2004089967 | 10/2004 |
| WO | WO 2005012242 | 2/2005 |
| WO | WO 2005012243 | 2/2005 |
| WO | WO 2005012318 | 2/2005 |
| WO | WO 2005034878 | 4/2005 |
| WO | WO 2005080549 | 9/2005 |
| WO | WO 2006002233 | 1/2006 |
| WO | WO 2006005682 | 1/2006 |
| WO | WO 2006011469 | 2/2006 |
| WO | WO 2006011502 | 2/2006 |
| WO | WO 2006037335 | 4/2006 |
| WO | WO 2006037537 | 4/2006 |
| WO | WO 2006050501 | 5/2006 |

OTHER PUBLICATIONS

Handlon, A.L. *Expert Opin Therapeutic Patents* 15(11):1531-1540 (2005).
Hoos, R., et al., *Helvetica Chimica Acta* 79(7):1757-1784 (1996).
Kerns, R.J., et al. *Tetrahedron Letters* 44(44):8069-8072 (2003).
Komoroski, B., et al., *American Diabetes Association Meeting*, Abstract 0188-OR (2007).
Whaley, J,. et al., *American Diabetes Association Meeting*, Abstract 0559-P (2007).
Wright, E.M. and Turk, E., *Eur J Physiol* 447:510-518 (2004).
Search Report and Written Opinion for Corresponding International Application PCT/US2007/079654, dated Nov. 4, 2008.
U.S. Appl. No. 61/309,592, filed Mar. 2, 2010, Brown.

* cited by examiner

INHIBITORS OF SODIUM GLUCOSE CO-TRANSPORTER 2 AND METHODS OF THEIR USE

This application claims priority to U.S. provisional application Nos. 60/848,156, filed Sep. 29, 2006, 60/905,714, filed Mar. 8, 2007, and 60/948,780, filed Jul. 10, 2007, the entireties of which are incorporated herein by reference.

1. FIELD OF THE INVENTION

This invention relates to methods of treating metabolic diseases and disorders such as diabetes, and to compounds and pharmaceutical compositions useful therein.

2. BACKGROUND

The sodium glucose co-transporter 2 (SGLT2) is a transporter that reabsorbs glucose from the renal filtrate and prevents the loss of glucose in the urine. Because competitive inhibitors of SGLT2 cause the renal excretion of glucose, they may be used to normalize high blood glucose levels associated with diseases such as diabetes. Handlon, A. L., *Expert Opin. Ther. Patents* 15(11):1531-1540 (2005).

A number of SGLT2 inhibitors have been disclosed. See, e.g., Handlon, supra; U.S. Pat. No. 6,515,117; U.S. patent application publication nos. US 2006/0035841, US 2004/0138439. At least one inhibitor is in clinical development as a treatment for Type 2 diabetes mellitus. See, e.g., Komoroski, B., et al., "Dapagliflozin (BMS-512148), a Selective Inhibitor of the Sodium-Glucose Uptake Transporter 2 (SGLT2), Reduces Fasting Serum Glucose and Glucose Excursion in Type 2 Diabetes Mellitus Patients Over 14 Days" *American Diabetes Assn. 67th Scientific Sessions*, Abstract 0188-OR (2007).

The first known SGLT2 inhibitor was the natural product phlorizin (glucose, 1-[2-(β-D-glucopyranosyloxy)-4,6-dihydroxyphenyl]-3-(4-hydroxyphenyl)-1-propanone), and "all subsequent SGLT2 inhibitors have been glycosides derived from its structure." Handlon, supra, at 1533. Phlorizin consists of a glucose moiety and two hydroxylated aromatic rings joined by a propanone spacer. Ehrenkranz, J. R. L., et al., *Diabetes Metab. Res. Rev.* 21:31-38 (2005). A review of the patent literature does not reveal any synthetic SGLT2 inhibitors that do not contain a glucoside moiety or a derivative thereof. Handlon, supra. In fact, "because of the relative uniformity of the glycosides in the SGLT2 patent literature, it has become increasingly difficult for potential drug inventors to find unexplored chemical space." Id. at 1537. But attempts are still being made. See, e.g., U.S. patent application Ser. Nos. 11/168,905 to Eckhardt et al., entitled "D-Xylopyranosyl-Substituted Phenyl Derivatives, Medicaments Containing Such Compounds, Their Use and Process for Their Manufacture;" 11/182,986 to Eckhardt et al., entitled "Methylidene-D-Xylopyranosyl- and Oxo-D-Xylopyranosyl-Substituted Phenyl Derivatives, Medicaments Containing Such Compounds, Their Use and Process for Their Manufacture;" and 11/199,962 to Eckhardt et al., entitled "D-Xylopyranosyl-Phenyl-Substituted Cycles, Medicaments Containing Such Compounds, Their Use and Process for Their Manufacture."

3. SUMMARY OF THE INVENTION

This invention encompasses novel SGLT2 inhibitors. One embodiment of the invention encompasses compounds of the formula:

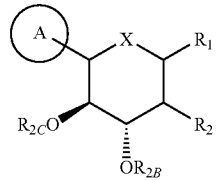

I and pharmaceutically acceptable salts and solvates thereof, wherein: A is optionally substituted aryl, cycloalkyl, or heterocycle; X is O, S or $NR_3$; when X is O, $R_1$ is $OR_{1A}$, $SR_{1A}$, $SOR_{1A}$, $SO_2R_{1A}$ or $N(R_{1A})_2$; when X is S, $R_1$ is hydrogen, $OR_{1A}$, $SR_{1A}$, $SOR_{1A}$, or $SO_2R_{1A}$; when X is $NR_3$, $R_1$ is $OR_{1A}$, $SR_{1A}$, $SOR_{1A}$, $SO_2R_{1A}$, or $R_{1A}$; each $R_{1A}$ is independently hydrogen or optionally substituted alkyl, aryl or heterocycle; $R_2$ is fluoro or $OR_{2A}$; each of $R_{2A}$, $R_{2B}$, and $R_{2C}$ is independently hydrogen, optionally substituted alkyl, C(O)alkyl, C(O)aryl or aryl; $R_3$ is hydrogen, $C(O)R_{3A}$, $CO_2R_{3A}$, $CON(R_{3B})_2$, or optionally substituted alkyl, aryl or heterocycle; each $R_{3A}$ is independently optionally substituted alkyl or aryl; and each $R_{3B}$ is independently hydrogen or optionally substituted alkyl or aryl.

Another embodiment encompasses compounds of the formula:

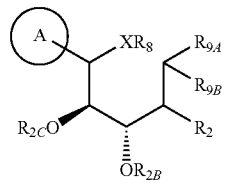

II and pharmaceutically acceptable salt or solvate thereof, wherein: A is optionally substituted aryl, cycloalkyl, or heterocycle; X is O or $NR_3$; $R_2$ is fluoro or $OR_{2A}$; each of $R_{2A}$, $R_{2B}$, and $R_{2C}$ is independently hydrogen, optionally substituted alkyl, C(O)alkyl, C(O)aryl or aryl; $R_3$ is hydrogen or optionally substituted alkyl, aryl or heterocycle; $R_8$ is hydrogen or $C(O)R_{8A}$; $R_{8A}$ is hydrogen or optionally substituted alkyl, alkoxy or aryl; $R_{9A}$ and $R_{9B}$ are each independently $OR_{9C}$ or $SR_{9C}$, or are taken together to provide O, S or $NR_{9C}$; and each $R_{9C}$ is independently optionally substituted alkyl, aryl or heterocycle.

The invention encompasses pharmaceutical compositions comprising the compounds disclosed herein. The invention also encompasses methods of inhibiting SGLT2 activity, as well as methods of treating, preventing and managing a variety of diseases and disorders.

4. BRIEF DESCRIPTION OF THE FIGURE

Certain aspects of this invention can be understood with reference to FIG. 1, which shows the effect of various compounds of the invention on the urine glucose excretion of mice. The compounds were orally dosed at 30 mg/kg.

5. DETAILED DESCRIPTION

This invention is based, in part, on the discovery that compounds of the formulae:

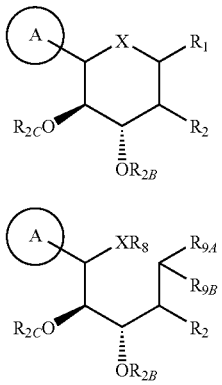

the substituents of which are defined below, can inhibit the sodium glucose co-transporter 2 (SGLT2).

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, °Ctyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzo-quinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "inhibits SGLT2 in vivo" means the inhibition of SGLT2 as determined using the in vivo assay described in the Examples, below.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences,* 18th ed. (Mack Publishing, Easton Pa.: 1990) and *Remington: The Science and Practice of Pharmacy,* 19th ed. (Mack Publishing, Easton Pa.: 1995).

Unless otherwise indicated, a "potent SGLT2 inhibitor" is a compound that has a SGLT2 $IC_{50}$ of less than about 500 nM.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "selective SGLT2 inhibitor" is a compound that has a SGLT1 $IC_{50}$ that is at least 10 times greater than its SGLT2 $IC_{50}$.

Unless otherwise indicated, the term "SGLT1 $IC_{50}$" is the $IC_{50}$ of a compound determined using the in vitro human SGLT1 inhibition assay described in the Examples, below.

Unless otherwise indicated, the term "SGLT2 $IC_{50}$" is the $IC_{50}$ of a compound determined using the in vitro human SGLT2 inhibition assay described in the Examples, below.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkyl-NHC(O)alkyl), amidinyl (—C(NH)NH-alkyl- or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Compounds

One embodiment of this invention encompasses compounds of the formula:

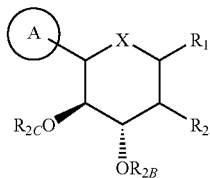

I and pharmaceutically acceptable salts and solvates thereof, wherein: A is optionally substituted aryl, cycloalkyl, or heterocycle; X is O, S or $NR_3$; when X is O, $R_1$ is $OR_{1A}$, $SR_{1A}$, $SOR_{1A}$, $SO_2R_{1A}$ or $N(R_{1A})_2$; when X is S, $R_1$ is hydrogen, $OR_{1A}$, $SR_{1A}$, $SOR_{1A}$, or $SO_2R_{1A}$; when X is $NR_3$, $R_1$ is $OR_{1A}$, $SR_{1A}$, $SOR_{1A}$, $SO_2R_{1A}$, or $R_{1A}$; each $R_{1A}$ is independently hydrogen or optionally substituted alkyl, aryl or heterocycle; $R_2$ is fluoro or $OR_{2A}$; each of $R_{2A}$, $R_{2B}$, and $R_{2C}$ is independently hydrogen, optionally substituted alkyl, C(O)alkyl, C(O)aryl or aryl; $R_3$ is hydrogen, $C(O)R_{3A}$, $CO_2R_{3A}$, $CON(R_{3B})_2$, or optionally substituted alkyl, aryl or heterocycle; each $R_{3A}$ is independently optionally substituted alkyl or aryl; and each $R_{3B}$ is independently hydrogen or optionally substituted alkyl or aryl.

Particular compounds are of the formula:

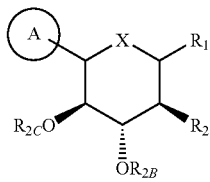

Some are of the formula:

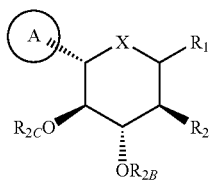

Some are of the formula:

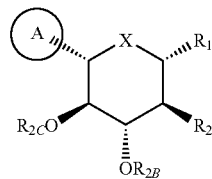

One embodiment of the invention encompasses compounds of the formula:

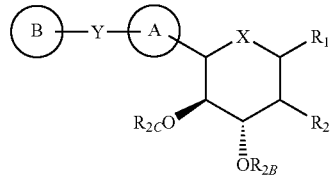

and pharmaceutically acceptable salts and solvates thereof, wherein: A is optionally substituted aryl, cycloalkyl, or heterocycle; B is optionally substituted aryl, cycloalkyl, or heterocycle; X is O, S or $NR_3$; Y is O, S, SO, $SO_2$, $NR_4$, $(C(R_5)_2)_p$, $(C(R_5)_2)_q$—C(O)—$(C(R_5)_2)_q$, $(C(R_5)_2)_q$—C(O)O—$(C(R_5)_2)_q$, $(C(R_5)_2)_q$—OC(O)—$(C(R_5)_2)_q$, $(C(R_5)_2)_q$—C(O)$NR_4$—$(C(R_5)_2)_q$, $(C(R_5)_2)_q$—$NR_4C(O)$—$(C(R_5)_2)_q$, or $(C(R_5)_2)_q$—$NR_4C(O)NR_4$—$(C(R_5)_2)_q$; when X is O, $R_1$ is $OR_{1A}$, $SR_{1A}$, $SOR_{1A}$, $SO_2R_{1A}$ or $N(R_{1A})_2$; when X is S, $R_1$ is hydrogen, $OR_{1A}$, $SR_{1A}$, $SOR_{1A}$, or $SO_2R_{1A}$; when X is $NR_3$, $R_1$ is $OR_{1A}$, $SR_{1A}$, $SOR_{1A}$, $SO_2R_{1A}$, or $R_{1A}$; each $R_{1A}$ is independently hydrogen or optionally substituted alkyl, aryl or heterocycle; $R_2$ is fluoro or $OR_{2A}$; each of $R_{2A}$, $R_{2B}$, and $R_{2C}$ is independently hydrogen, optionally substituted alkyl, C(O)alkyl, C(O)aryl, or aryl; $R_3$ is hydrogen, $C(O)R_{3A}$, $CO_2R_{3A}$, $CON(R_{3B})_2$, or optionally substituted alkyl, aryl or heterocycle; each $R_{3A}$ is independently optionally substituted alkyl or aryl; each $R_{3B}$ is independently hydrogen or optionally substituted alkyl or aryl; each $R_4$ is independently hydrogen or optionally substituted alkyl; each $R_5$ is independently hydrogen, hydroxyl, halogen, amino, cyano, $OR_{5A}$, $SR_{5A}$, or optionally substituted alkyl; each $R_{5A}$ is independently optionally substituted alkyl; p is 0-3; and each q is independently 0-2.

Particular compounds are of the formula:

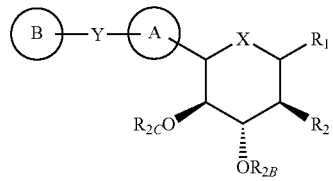

Some are of the formula:

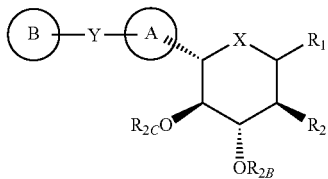

Some are of the formula:

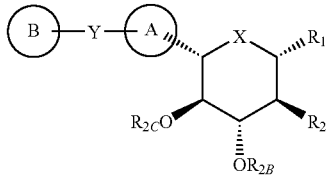

Some are of the formula:

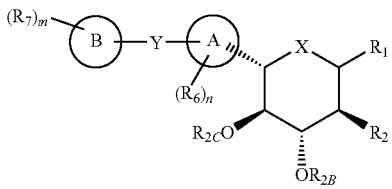

wherein: each $R_6$ is independently hydrogen, hydroxyl, halogen, amino, cyano, nitro, $C\equiv CR_{6A}$, $OR_{6A}$, $SR_{6A}$, $SOR_{6A}$, $SO_2R_{6A}$, $C(O)R_{6A}$, $CO_2R_{6A}$, $CO_2H$, $CON(R_{6A})(R_{6A})$, $CONH(R_{6A})$, $CONH_2$, $NHC(O)R_{6A}$, $NHSO_2R_{6A}$, or optionally substituted alkyl, aryl or heterocycle; each $R_{6A}$ is independently optionally substituted alkyl, aryl or heterocycle; each $R_7$ is independently hydrogen, hydroxyl, halogen, amino, cyano, nitro, $C\equiv CR_{7A}$, $OR_{7A}$, $SR_{7A}$, $SOR_{7A}$, $SO_2R_{7A}$, $C(O)R_{7A}$, $CO_2R_{7A}$, $CO_2H$, $CON(R_{7A})(R_{7A})$, $CONH(R_{7A})$, $CONH_2$, $NHC(O)R_{7A}$, $NHSO_2R_{7A}$, or optionally substituted alkyl, aryl or heterocycle; each $R_{7A}$ is independently optionally substituted alkyl, aryl or heterocycle; m is 1-3; and n is 1-3.

Some are of the formula:

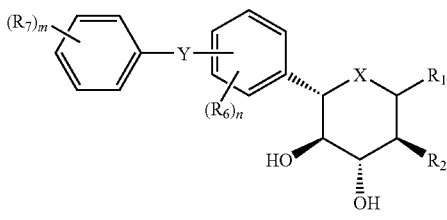

Some are of the formula:

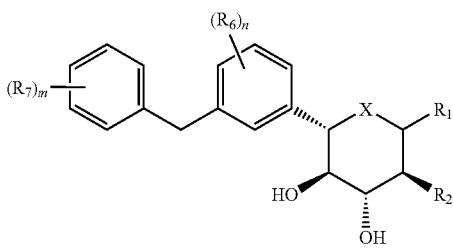

Some are of the formula:

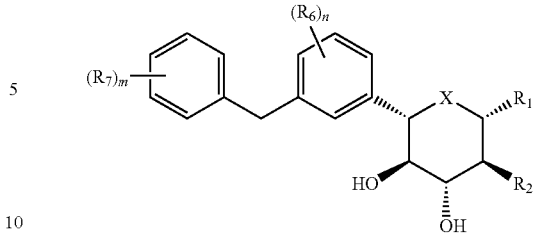

One embodiment of the invention encompasses compounds of the formula:

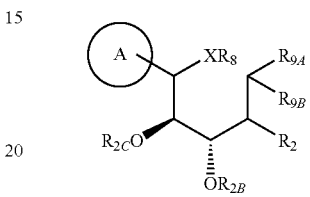

II and pharmaceutically acceptable salts and solvates thereof, wherein: A is optionally substituted aryl, cycloalkyl, or heterocycle; X is O or $NR_3$; $R_2$ is fluoro or $OR_{2A}$; each of $R_{2A}$, $R_{2B}$, and $R_{2C}$ is independently hydrogen, optionally substituted alkyl, C(O)alkyl, C(O)aryl or aryl; $R_3$ is hydrogen or optionally substituted alkyl, aryl or heterocycle; $R_8$ is hydrogen or $C(O)R_{8A}$; $R_{8A}$ is hydrogen or optionally substituted alkyl, alkoxy or aryl; $R_{9A}$ and $R_{9B}$ are each independently $OR_{9C}$ or $SR_{9C}$, or are taken together to provide O, S or $NR_{9C}$; and each $R_{9C}$ is independently optionally substituted alkyl, aryl or heterocycle.

With regard to the various formulae disclosed herein, as applicable, particular compounds of the invention are such that A is optionally substituted 6-membered aryl or heterocycle. In others, A is optionally substituted 5-membered heterocycle. In some, A is an optionally substituted fused bicyclic heterocycle.

In some, B is optionally substituted 6-membered aryl or heterocycle. In others, B is optionally substituted 5-membered heterocycle. In others, B is an optionally substituted fused bicyclic heterocycle.

In some, X is O. In others, X is S. In others, X is $NR_3$.

In some, Y is $(C(R_4)_2)_p$ and, for example, p is 1. In some, Y is $(C(R_5)_2)_q$—$C(O)$—$(C(R_5)_2)_q$ and, for example, each q is independently 0 or 1.

In some, $R_1$ is $OR_{1A}$. In others, $R_1$ is $SR_{1A}$. In others, $R_1$ is $SOR_{1A}$. In others, $R_1$ is $SO_2R_{1A}$. In others, $R_1$ is $N(R_{1A})_2$. In others, $R_1$ is hydrogen. In others, $R_1$ is $R_{1A}$.

In some, $R_{1A}$ is hydrogen. In others, $R_{1A}$ is optionally substituted alkyl (e.g., optionally substituted lower alkyl).

In some, $R_2$ is fluoro. In others, $R_2$ is $OR_{2A}$.

In some, $R_{2A}$ is hydrogen.

In some, $R_{2B}$ is hydrogen.

In some, $R_{2C}$ is hydrogen.

In some, $R_3$ is hydrogen. In others, $R_3$ is optionally substituted lower alkyl (e.g., optionally substituted methyl).

In some, $R_4$ is hydrogen or optionally substituted lower alkyl.

In some, each $R_5$ is hydrogen or optionally substituted lower alkyl (e.g., methyl, ethyl, $CF_3$).

In some, $R_6$ is hydrogen, hydroxyl, halogen, $OR_{6A}$ or optionally substituted lower alkyl (e.g., optionally halogenated methyl, ethyl, or isopropyl). In some, $R_6$ is hydrogen. In some, $R_6$ is halogen (e.g., chloro). In some, $R_6$ is hydroxyl. In some, $R_6$ is $OR_{6A}$ (e.g., methoxy, ethoxy). In some, $R_6$ is optionally substituted methyl (e.g., $CF_3$).

In some, $R_7$ is hydrogen, $C\equiv CR_{7A}$, $OR_{7A}$ or optionally substituted lower alkyl (e.g., optionally halogenated methyl, ethyl, or isopropyl). In some, $R_7$ is hydrogen. In some, $R_7$ is $C\equiv CR_{7A}$ and $R_{7A}$ is, for example, optionally substituted (e.g., with lower alkyl or halogen) monocyclic aryl or heterocycle. In some, $R_7$ is $OR_{7A}$ (e.g., methoxy, ethoxy). In some, $R_7$ is acetylenyl or optionally substituted methyl or ethyl.

Particular compounds of the invention are of the formula:

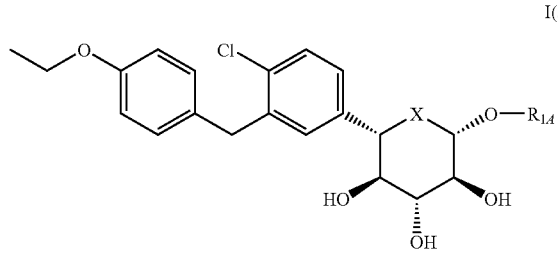
I(a)

Others are of the formula:

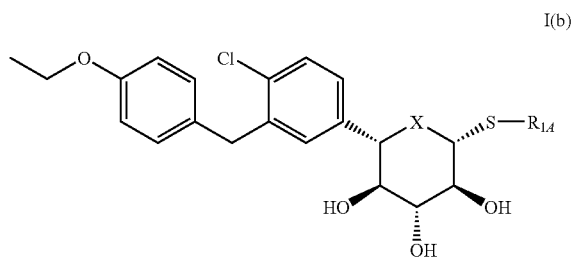
I(b)

Others are of the formula:

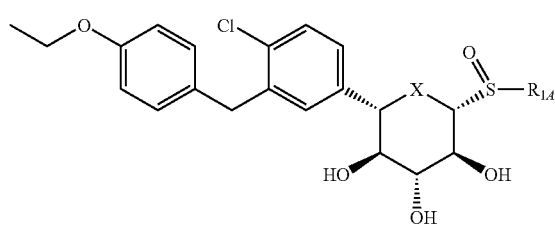
I(c)

Others are of the formula:

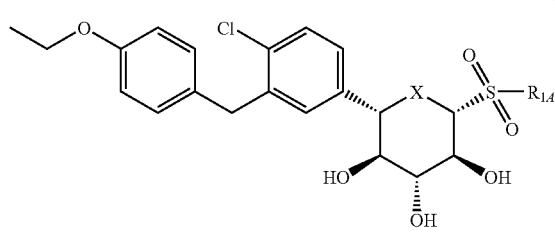
I(d)

Others are of the formula:

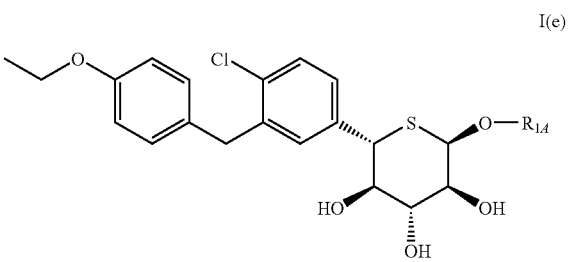
I(e)

Others are of the formula:

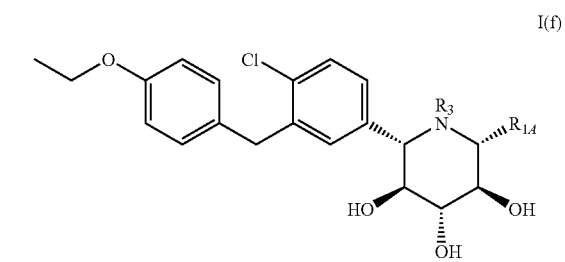
I(f)

In particular compounds of formulae I(a)-(d), X is O. In others, X is S. In others, X is $NR_3$ and $R_3$ is, for example, hydrogen. In particular compounds of formulae I(a)-(f), $R_{1A}$ is hydrogen. In others, $R_{1A}$ is optionally substituted methyl or ethyl.

Preferred compounds are potent SGLT2 inhibitors. Particular compounds have a SGLT2 $IC_{50}$ of less than about 500, 400, 300, 250, 200, 150, 100, 75, 50 or 25 nM.

Particular compounds are selective SGLT2 inhibitors. For example, certain compounds have a SGLT1 $IC_{50}$ that is at least 10, 15, 20, 25, 50, 75 or 100 times greater than their SGLT2 $IC_{50}$.

5.3. Methods of Synthesis

Compounds of the invention may be prepared by methods known in the art and by those described herein. For example, compounds may be prepared by methods such as that shown below in Scheme 1:

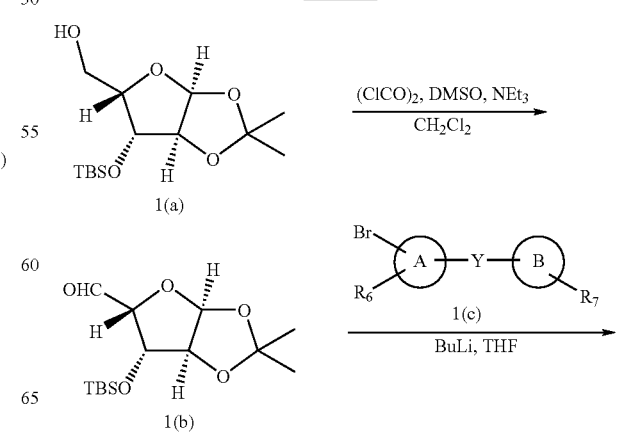

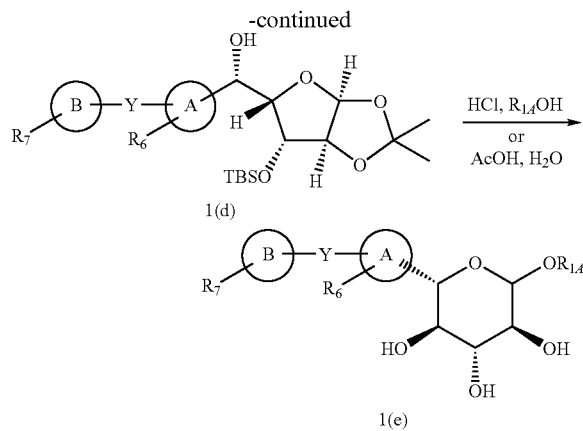

In this method, known alcohol 1(a) (see, e.g., *Nucleosides Nucleotides*, 20:649-652 (2001)) is oxidized under suitable conditions (e.g., with an oxidant such as oxalyl chloride in DMSO) to form aldehyde 1(b). Treatment of a bromide of formula 1(c) with an agent such as butyl lithium or magnesium bromide followed by addition to aldehyde 1(b) produces alcohol 1(d). Treatment of that compound with an alcohol or water under acidic conditions produces compound 1(e). If desired, methods well known in the art may be used to transform compound 1(e) into various other compounds encompassed by this invention (e.g., compounds of formula I, wherein one or more of $R_{2A}$, $R_{2B}$ and $R_{2C}$ is not hydrogen, and/or $R_1$ is $SR_{1A}$ or $NHR_{1A}$).

With regard to scheme 1 and other synthetic approaches described herein, methods of preparing the A and A-Y—B moieties are well known, as are methods of their use to prepare SGLT2 inhibitors. For example, the synthesis of linked diaryl derivatives in the preparation of SGLT2 inhibitors is described in U.S. Pat. Nos. 7,045,665 and 7,053,060; in U.S. patent application Ser. Nos. 10/735,179; 10/745,075; 11/080,150; and 11/182,986; and in international patent application nos. WO 2006/006496 and WO 2006/089872.

The synthesis of SGLT2 inhibitors containing linked phenyl-carbocycle moieties is described, for example, in U.S. patent application Ser. Nos. 11/190,315 and 11/199,962.

The synthesis of linked heterocycles and their use to provide SGLT2 inhibitors is described, for example, in U.S. patent application Ser. Nos. 10/540,519; 10/734,573; 11/247,216; 11/247,356; and in international patent application nos. WO 03/020737; WO 2004/058790; WO 2004/080990; WO 2004/089967; WO 2005/011592; WO 2005/012242; WO 2005/012243; WO 2005/012318; WO 2005/021566; and WO 2005/085265.

Piperidine-based compounds may be prepared by methods such as that shown below in Scheme 2:

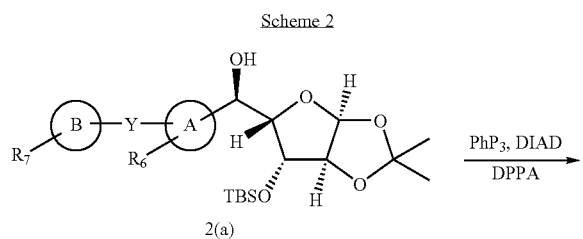

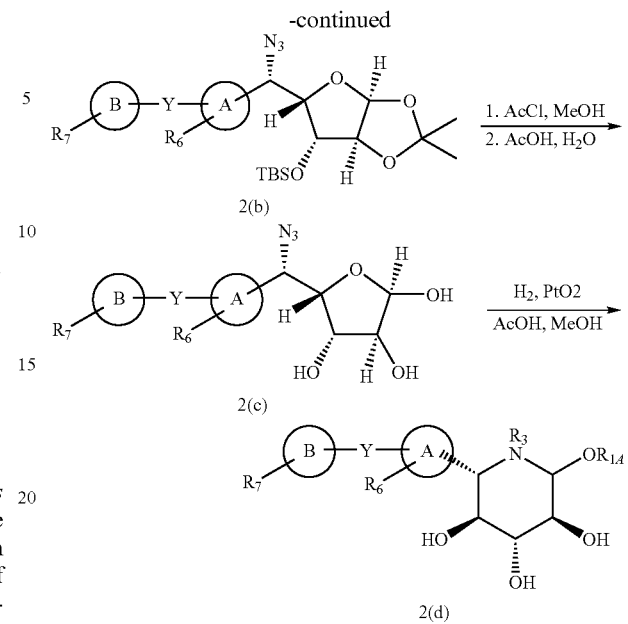

In this method, compound 2(a), which may be prepared as shown in Scheme 1, is contacted with an azide (e.g., diphenylphosphoryl azide) under conditions sufficient to provide the azide 2(b). The azide is then treated under acidic conditions to provide the deprotected furan 2(c), which is subsequently treated with a reducing agent (e.g., hydrogen in the presence of platinum oxide) under acidic conditions to provide compound 2(d). If desired, methods well known in the art may be used to transform compound 2(d) into various other compounds encompassed by this invention (e.g., compounds of formula I, wherein one or more of $R_{2A}$, $R_{2B}$ and $R_{2C}$ is not hydrogen, and/or $R_1$ is $SR_{1A}$ or $NHR_{1A}$).

Tetrahydrothiopyran-based compounds may be prepared as shown below in Scheme 3:

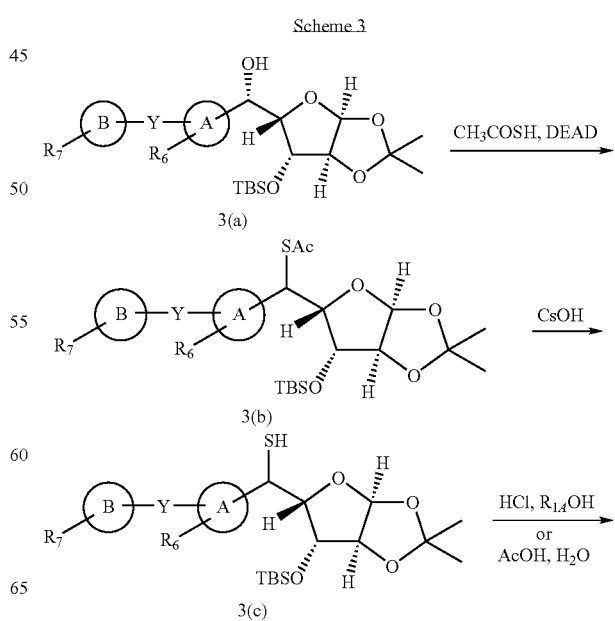

-continued

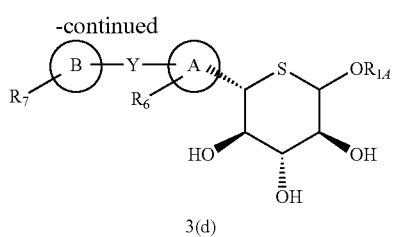

3(d)

In this method, compound 3(a), which may be prepared as shown in Scheme 1, is contacted with a suitable sulfur-containing compound (e.g., thioacetate) under suitable conditions (e.g., in the presence of diethylazodicarboxylate) to form thioacetate 3(b). The thioacetate is then treated with a suitable base (e.g., cesium hydroxide) to provide the thiol of formula 3(c), which is subsequently treated with an alcohol or water under acidic conditions to provide compound 3(d). If desired, methods well known in the art may be used to transform compound 3(d) into various other compounds encompassed by this invention (e.g., compounds of formula I, wherein one or more of $R_{2A}$, $R_{2B}$ and $R_{2C}$ is not hydrogen, and/or $R_1$ is $SR_{1A}$ or $NHR_{1A}$).

Compounds comprising a fluoronated sugar or sugar analogue (compounds of formula I, wherein $R_2$ is F) may be prepared from the correspondingly substituted starting materials using methods known in the art. See, e.g., U.S. patent application Ser. No. 10/735,179.

Open-form compounds (e.g., compounds of formula II) are readily prepared by methods known in the art. For example, they may be prepared using approaches such as that shown below in Scheme 4:

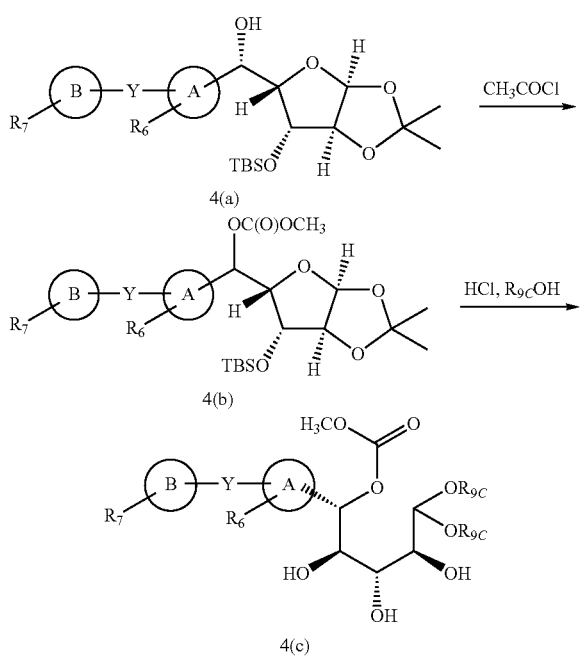

In this method, compound 4(a), which may be prepared as shown in Scheme 1, is contacted with a reactive compound (e.g., methylchloroformate) under suitable conditions to form methyl carbonate 4(b). The methyl carbonate is then treated with an alcohol under acidic conditions to provide compound 4(c). If desired, methods well known in the art may be used to transform compound 4(c) into various other compounds encompassed by this invention (e.g., compounds of formula II, wherein one or more of $R_{2A}$, $R_{2B}$ and $R_{2C}$ is not hydrogen).

Using methods known in the art, the synthetic approaches shown above are readily modified to obtain a wide range of compounds. And chiral chromatography and other well-known techniques may be used to obtain stereomerically pure compounds. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, NY, 1962); and Wilen, S. H., *Tables of Resolving Agents and Optical Resolutions*, p. 268 (E. L. Eliel, Ed., Univ. of Notre Dame Press, Notre Dame, Ind., 1972). In addition, syntheses may utilize chiral starting materials to yield stereomerically enriched or pure products.

5.4. Methods of Use

This invention encompasses a method of inhibiting SGLT2 activity, which comprises contacting SGLT2 with an effective amount of a compound of the invention (i.e., a novel compound disclosed herein). In one embodiment, the protein is in vivo. In another, it is ex vivo.

The invention also encompasses a method of decreasing blood glucose in a patient (e.g., a mammal, such as a human, dog or cat), which comprises administering to the patient an effective amount of a compound of the invention.

The invention also encompasses a method of increasing the excretion of glucose in the urine of a patient, which comprises administering to the patient an effective amount of a compound of the invention.

The invention also encompasses a method of restoring or increasing insulin sensitivity in a patient, which comprises administering to the patient an effective amount of a compound of the invention.

The invention also encompasses a method of treating, managing or preventing a disease or disorder in a patient, which comprises administering to the patient a therapeutically or prophylactically effective amount of a compound of the invention. Examples of diseases and disorders include atherosclerosis, cardiovascular disease, diabetes (Type 1 and 2), hyperglycaemia, hypertension, lipid disorders, obesity, and Syndrome X. A particular disease is type 2 diabetes.

The amount, route of administration and dosing schedule of a compound may depend upon factors such as the specific indication to be treated, prevented or managed, and the age, gender and condition of the patient. The roles played by such factors are well known in the art, and may be accommodated by routine experimentation.

5.5. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18$^{th}$ ed. (Mack Publishing, Easton Pa.: 1990).

Pharmaceutical compositions of this invention are preferably administered orally. Discrete dosage forms suitable for oral administration include tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences*, 18$^{th}$ ed. (Mack Publishing, Easton Pa.: 1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

6. EXAMPLES

Aspects of this invention can be understood from the following examples, which do not limit its scope.

6.1. Example 1

Synthesis of (2S,3R,4R,5S)-2-[4-Chloro-3-(4-ethoxy-benzyl)-phenyl]-6-methoxy-tetrahydro-pyran-3,4,5-triol

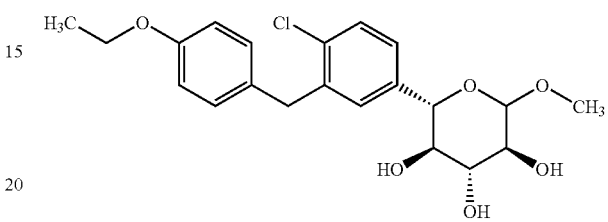

The captioned compound was prepared in several steps.

A. Preparation of [(3aS,5S,6R,6aS)-6-(tert-butyl-dimethyl-silanyloxy)-2,2-dimethyl-tetrahydro-furo[2,3-d][113]dioxol-5-yl]-methanol. This compound was synthesized using procedures known in the art. See, e.g., *Nucleosides Nucleotides*, 20:649-652 (2001) and references therein.

B. Preparation of (3aS,5R,6R,6aS)-6-(tert-butyl-dimethyl-silanyloxy)-2,2-dimethyl-tetrahydro-furo[2,3-d][133]dioxole-5-carbaldehyde. To a solution of oxalyl chloride (0.76 ml, 8.7 mmol) in CH$_2$Cl$_2$ (55 ml) under N$_2$ at −78° C. was added dropwise a solution of DMSO (0.84 ml, 11.8 mmol) in CH$_2$Cl$_2$ (5 ml). After 15 minutes, the alcohol from step A (2.40 g, 7.9 mmol) in CH$_2$Cl$_2$ (20 ml) was added dropwise. After 15 minutes, NEt$_3$ was added slowly. The reaction was allowed to warm slowly to room temperature over 105 minutes, then quenched with H$_2$O, diluted with Et$_2$O, and washed with H$_2$O, sat aq. NaHCO$_3$, and brine. The combined organic phases were back extracted with Et$_2$O, which was washed by the same sequence. The combined organic phases were dried of MgSO$_4$, filtered, and concentrated under vacuum to give (3aS,5R,6R,6aS)-6-(tert-butyl-dimethyl-silanyloxy)-2,2-dimethyl-tetrahydro-furo[2,3-d][1,3]dioxole-5-carbaldehyde (2.4 g, about 64% clean by NMR). The product was carried on without further purification.

C. Preparation of 4-bromo-1-chloro-2-(4-ethoxy-benzyl)-benzene. This compound was prepared as described in U.S. patent application Ser. No. 10/745,075 to Deshpande et al., filed Dec. 23, 2003.

D. Preparation of (S)-[(3aS,5S,6R,6aS)-6-(tert-butyl-dimethyl-silanyloxy)-2,2-dimethyl-tetrahydro-furo[2,3-d][1,3]dioxol-5-yl]-[4-chloro-3-(4-ethoxy-benzyl)-phenyl]-methanol. To a solution of 4-bromo-1-chloro-2-(4-ethoxy-benzyl)-benzene from step C (3.6 g, 11.1 mmol) in THF (60 ml) under N$_2$ at −78° C. was added dropwise BuLi (2.5 M in hexanes, 4.4 ml, 11.1 mmol). After 30 minutes, aldehyde from step B (2.4 g, 64% clean, 5.1 mmol) in THF (20 ml) was added dropwise, and the reaction was stirred for 30 min at −78° C., allowed to warm to room temperature and stirred for 60 minutes, quenched with sat. aq. NH$_4$Cl, diluted with Et$_2$O, and washed with H$_2$O and brine. The combined aqueous washes were back extracted with Et$_2$O, which was washed by the same sequence. The combined organic extracts were dried over MgSO$_4$, filtered, and concentrated under vacuum. The residue was purified by flash chromatography (120 g SiO$_2$, 0-20% EtOAc: Hexanes, 75 minutes, 85 ml/min) to give clean (S)-[(3aS,5S,6R,6aS)-6-(tert-butyl-dimethyl-silanyloxy)-2,2-dimethyl-tetrahydro-furo[2,3-d][1,3]dioxol-5-yl]-[4-chloro-3-(4-ethoxy-benzyl)-phenyl]-methanol (0.84 g, 1.5 mmol, 30%) plus the C5 epimer (0.83 g) and some mixed fractions (0.51 g).

$^1$H NMR (400 MHz, Chloroform-d) δ ppm: 7.37 (d, J=8.34 Hz, 1H), 7.18-7.23 (m, 1H), 7.15 (d, J=2.02 Hz, 1H), 7.06-7.11 (m, 2H), 6.80-6.84 (m, 2H), 5.99 (d, J=3.79 Hz, 1H), 5.21 (d, J=2.78 Hz, 1H), 5.11 (d, J=2.53 Hz, 1H), 4.46 (d, J=3.54 Hz, 1H), 3.97-4.10 (m, 5H), 3.95 (t, J=2.65 Hz, 1H), 1.38-1.44 (m, 6H), 1.30 (s, 3H), 0.84 (s, 9H), 0.10 (s, 3H), −0.08 (s, 3H).

E. Preparation of (2S,3R,4R,5S)-2-[4-chloro-3-(4-ethoxy-benzyl)-phenyl]-6-methoxy-tetrahydro-pyran-3,4,5-triol. A solution of 0.35 M HCl in MeOH was prepared by adding AcCl (0.25 ml, 3.5 mmol) to MeOH (10 ml) and stirring for 15 minutes The alcohol from step D (0.84 g, 1.5 mmol) was treated with this solution for 16 hours at room temperature and 2 hours at 80° C. in a sealed vial. The reaction was cooled to room temperature, quenched with $K_2CO_3$ until basic, diluted with $CH_2Cl_2$, filtered, and concentrated under vacuum. The product was purified by flash chromatography (40 g $SiO_2$, 0-10% MeOH: $CH_2Cl_2$, 60 minutes, 35 ml/min), suspended in $H_2O$, and lyophilized to give (2S,3R,4R,5S)-2-[4-chloro-3-(4-ethoxy-benzyl)-phenyl]-6-methoxy-tetrahydro-pyran-3,4,5-triol (0.46 g, 1.1 mmol, 75%) as a white solid. NMR revealed a 1.2:1 ratio of α and β anomers.

$^1$H NMR (400 MHz, Chloroform-d) δ ppm: 7.38-7.42 (m, 1H), 7.22-7.26 (m, 2H), 7.11 (d, J=8.34 Hz, 2H), 6.81-6.85 (m, 2H), 4.86 (d, J=3.79 Hz, 1H α), 4.43 (d, J=9.85 Hz, 1H α), 4.34 (d, J=7.58 Hz, 1H β), 4.16 (d, J=9.35 Hz, 1H β), 3.99-4.12 (m, 4H), 3.80-3.86 (m, 1H α), 3.64-3.72 (m, 1H), 3.54 (s, 3H β), 3.46-3.54 (m, 1.5H), 3.45 (s, 3H α), 2.69 (d, J=2.53 Hz, 1H β), 2.62 (d, J=2.27 Hz, 1H α), 2.50 (d, J=2.27 Hz, 1H β), 2.12 (d, J=9.85 Hz, 1H α), 2.00 (d, J=3.03 Hz, 1H β), 1.98 (d, J=2.78 Hz, 1H α), 1.41 (t, J=6.95 Hz, 3H). MS (ES+) [M+NH$_4$]$^+$=426.

6.2. Example 2

Synthesis of (3S,4R,5R,6S)-6-[4-Chloro-3-(4-ethoxy-benzyl)-phenyl]-tetrahydro-pyran-2,3,4,5-tetraol

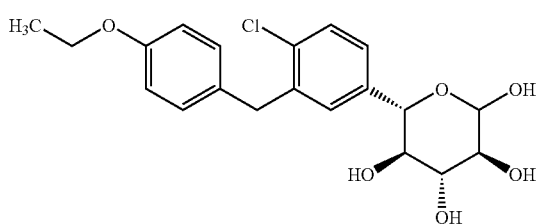

The alcohol from Example 1, step D (51 mg, 0.093 mmol) was treated with 1:1 AcOH:$H_2O$ (1 ml) at 80° C. in a sealed vial for 18 hours. The reaction was cooled to room temperature, diluted with EtOAc to transfer to a flask, and concentrated under vacuum. The residue was dissolved in $CH_2Cl_2$, treated with $NaHCO_3$ and $MgSO_4$ for 30 minutes, filtered, and concentrated under vacuum. The product was purified by flash chromatography (4 g $SiO_2$, 0-12% MeOH: $CH_2Cl_2$, 30 minutes, 10 ml/min), suspended in $H_2O$, and lyophilized to give (3S,4R,5R,6S)-6-[4-chloro-3-(4-ethoxy-benzyl)-phenyl]-tetrahydro-pyran-2,3,4,5-tetraol (31 mg, 0.079 mmol, 85%) as a white solid. NMR revealed a 1:1 ratio of α and β anomers.

$^1$H NMR (400 MHz, methanol-d$_4$) δ ppm 7.34 (dd, J=8.08, 4.04 Hz, 1H), 7.22-7.30 (m, 2H), 7.09 (d, J=8.34 Hz, 2H), 6.80 (d, J=8.08 Hz, 2H), 5.16 (d, J=3.79 Hz, 1H α), 4.65 (d, J=9.60 Hz, 1H α or β), 4.59 (d, J=7.58 Hz, 1H α or β), 4.14 (d, J=9.60 Hz, 1H α or β), 3.96-4.07 (m, 4H), 3.76 (t, J=9.35 Hz, 1H α or β), 3.50 (dd, J=9.60, 3.79 Hz, 1H α or β), 3.43 (t, J=9.09 Hz, 1H α or β), 3.23-3.29 (m, 1.5H), 1.36 (t, J=7.07 Hz, 3H). MS (ES+) [M+NH$_4$]$^+$=412.

6.3. Example 3

Synthesis of (2S,3R,4R,5S)-2-[4-Chloro-3-(4-ethoxy-benzyl)-phenyl]-6-ethoxy-tetrahydro-pyran-3,4,5-triol

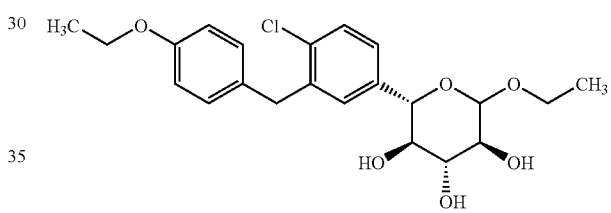

A solution of 0.35 M HCl in EtOH was prepared by adding AcCl (0.025 ml, 0.35 mmol) to EtOH (1 ml) and stirring for 15 minutes The alcohol from Example 1, step D (61 mg, 0.11 mmol) was treated with this solution for 2 hours at 80° C. in a sealed vial. The reaction cooled to room temperature, quenched with concentrated NH$_4$OH until basic, treated with NaHCO$_3$ for 30 minutes, diluted with $CH_2Cl_2$, filtered, and concentrated under vacuum. The product was purified by flash chromatography (4 g $SiO_2$, 0-10% MeOH: $CH_2Cl_2$, 40 minutes, 10 ml/min), suspended in $H_2O$, and lyophilized to give (2S,3R,4R,5S)-2-[4-chloro-3-(4-ethoxy-benzyl)-phenyl]-6-ethoxy-tetrahydro-pyran-3,4,5-triol (40 mg, 0.095 mmol, 85%) as a white solid. NMR revealed a 1.75:1 ratio of α and β anomers.

$^1$H NMR (400 MHz, Chloroform-d) δ ppm: 7.28-7.32 (m, 1H), 7.14 (m, 2H), 7.02 (d, J=8.84 Hz, 2H), 6.72-6.76 (m, 2H), 4.88 (d, J=4.04 Hz, 1H α), 4.37 (d, J=9.60 Hz, 1H α), 4.33 (d, J=7.83 Hz, 1H β), 4.06 (d, J=9.35 Hz, 1H β), 3.89-4.02 (m, 4H), 3.36-3.87 (m, 5H), 2.62 (s, 1H β), 2.54 (s, 1H α), 2.41 (d, J=1.52 Hz, 1H β), 2.02 (d, J=10.36 Hz, 1H α), 1.92 (d, J=2.53 Hz, 1H), 1.32 (t, J=6.95 Hz, 3H), 1.13-1.19 (m, 3H). MS (ES+) [M+NH$_4$]$^+$=440.

6.4. Example 4

Synthesis of (2S,3R,4R,5S,6S)-2-[4-Chloro-3-(4-ethoxy-benzyl)-phenyl]-6-isopropoxy-tetrahydro-pyran-3,4,5-triol and (2S,3R,4R,5S,6R)-2-[4-Chloro-3-(4-ethoxy-benzyl)-phenyl]-6-isopropoxy-tetrahydro-pyran-3,4,5-triol

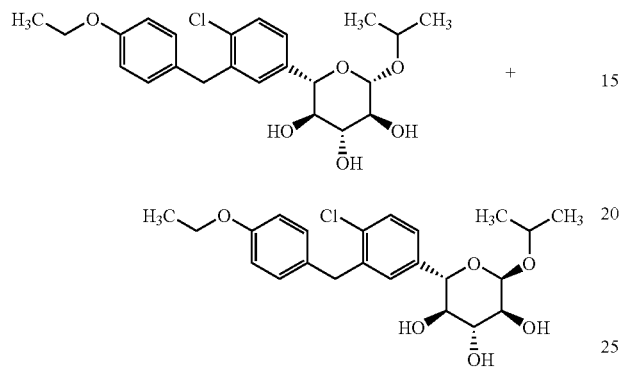

A solution of 0.35 M HCl in i-PrOH was prepared by adding AcCl (0.025 ml, 0.35 mmol) to i-PrOH (1 ml) and stirring for 15 minutes The alcohol from Example 1, step D (68 mg, 0.12 mmol) was treated with this solution for 2 hours at 80° C. in a sealed vial. The reaction cooled to room temperature, quenched with concentrated $NH_4OH$ until basic, treated with $NaHCO_3$ for 30 minutes, diluted with $CH_2Cl_2$, filtered, and concentrated under vacuum. The residue was purified by flash chromatography (4 g $SiO_2$, 0-10% MeOH:$CH_2Cl_2$, 40 minutes, 10 ml/min) to give 50 mg of material, which was further purified by prep HPLC (19×50 mm C18 column, 20-70% MeCN:$H_2O$ (10 mM $NH_4OAc$), 14 minutes, 30 ml/min) to give (2S,3R,4R,5S,6S)-2-[4-chloro-3-(4-ethoxy-benzyl)-phenyl]-6-isopropoxy-tetrahydro-pyran-3,4,5-triol (β anomer, 7 mg, 0.016 mmol) and (2S,3R,4R,5S,6R)-2-[4-chloro-3-(4-ethoxy-benzyl)-phenyl]-6-isopropoxy-tetrahydro-pyran-3,4,5-triol (α anomer, 25 mg, 0.057 mmol).

(2S,3R,4R,5S,6S)-2-[4-chloro-3-(4-ethoxy-benzyl)-phenyl]-6-isopropoxy-tetrahydro-pyran-3,4,5-triol: $^1$H NMR (400 MHz, Chloroform-d) δ ppm: 7.37-7.40 (m, 1H), 7.26 (m, 2H), 7.12 (d, J=8.59 Hz, 2H), 6.80-6.84 (m, 2H), 4.48 (d, J=7.83 Hz, 1H), 4.15 (d, J=9.35 Hz, 1H), 3.95-4.10 (m, 5H), 3.69 (t, J=9.09 Hz, 1H), 3.46-3.52 (m, 2H), 2.69 (br. s., 1H), 2.43 (br. s., 1H), 2.05 (br. s., 1H), 1.41 (t, J=7.07 Hz, 3H), 1.22 (t, J=6.57 Hz, 6H). MS (ES+) $[M+NH_4]^+$=454.

(2S,3R,4R,5S,6R)-2-[4-chloro-3-(4-ethoxy-benzyl)-phenyl]-6-isopropoxy-tetrahydro-pyran-3,4,5-triol: $^1$H NMR (400 MHz, Chloroform-d) δ ppm 7.39 (d, J=8.84 Hz, 1H), 7.22 (m, 2H), 7.11 (d, J=8.59 Hz, 2H), 6.80-6.85 (m, 2H), 5.04 (d, J=4.04 Hz, 1H), 4.51 (d, J=9.60 Hz, 1H), 3.98-4.10 (m, 4H), 3.93 (ddd, J=12.25, 6.32, 6.19 Hz, 1H), 3.82 (t, J=9.22 Hz, 1H), 3.62 (dd, J=9.47, 3.66 Hz, 1H), 3.49 (t, J=9.22 Hz, 1H), 2.03 (br s, 3H), 1.41 (t, J=6.95 Hz, 3H), 1.23 (d, J=6.32 Hz, 3H), 1.19 (d, J=6.06 Hz, 3H). MS (ES+) $[M+NH_4]^+$=454.

6.5. Example 5

Synthesis of (2S,3R,4R,5S,6R)-2-[4-Chloro-3-(4-ethoxy-benzyl)-phenyl]-6-methoxy-tetrahydro-pyran-3,4,5-triol and (2S,3R,4R,5S,6S)-2-[4-Chloro-3-(4-ethoxy-benzyl)-phenyl]-6-methoxy-tetrahydro-pyran-3,4,5-triol

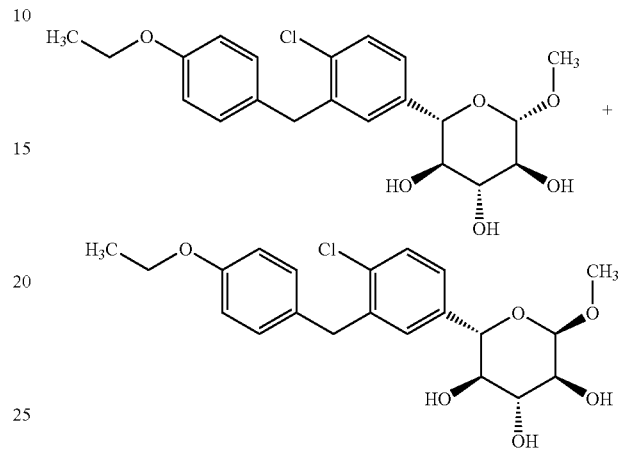

A sample of compound from Example 1 step E (80 mg) was dissolved in 4 ml of 30% ethanol/hexanes and injected in 400 μl portions onto a ChiralPak AD-H column (20×250 mm, 5.5 ml/min, 31.55% ethanol/hexane as eluent isocratic, ambient temperature, 30 min run) to separate the two isomers from each other. The first isomer (r.t. 23 min) was identified as the alpha isomer (6R, 20 mg) and the second (r.t. 26 minutes, 21 mg) was identified as the beta isomer (6S).

(2S,3R,4R,5S,6R)-2-[4-Chloro-3-(4-ethoxy-benzyl)-phenyl]-6-methoxy-tetrahydro-pyran-3,4,5-triol: $^1$H NMR (400 MHz, Chloroform-4) δ ppm 7.39 (d, J=8.84 Hz, 1H), 7.22-7.25 (m, 2H), 7.11 (d, J=8.59 Hz, 2H), 6.83 (d, J=8.59 Hz, 2H), 4.85 (d, J=4.04 Hz, 1H), 4.42 (d, J=9.60 Hz, 1H), 3.99-4.11 (m, 4H), 3.82 (t, J=9.22 Hz, 1H), 3.66 (br. s., 1H), 3.42-3.48 (m, 4H), 2.79 (br. s., 1H), 2.23 (d, J=1.26 Hz, 1H), 2.12 (br. s., 1H), 1.40 (t, J=6.95 Hz, 3H). MS (ES+) $[M+NH_4]^+$=426.

(2S,3R,4R,5S,6S)-2-[4-Chloro-3-(4-ethoxy-benzyl)-phenyl]-6-methoxy-tetrahydro-pyran-3,4,5-triol: $^1$H NMR (400 MHz, Chloroform-d) δ ppm 7.39 (d, J=8.59 Hz, 1H), 7.23-7.26 (m, 2H), 7.11 (d, J=8.84 Hz, 2H), 6.80-6.84 (m, 2H), 4.33 (d, J=7.58 Hz, 1H), 4.07-4.17 (m, 2H), 3.98-4.04 (m, 3H), 3.68 (t, J=9.09 Hz, 1H), 3.46-3.55 (m, 5H), 2.89 (br. s., 1H), 2.64 (br. s., 1H), 2.16 (br. s., 1H), 1.40 (t, J=7.07 Hz, 3H). MS (ES+) $[M+NH_4]^+$=426.

(2S,3R,4R,5S,6S)-2-[4-Chloro-3-(4-ethoxy-benzyl)-phenyl]-6-methoxy-tetrahydro-pyran-3,4,5-triol was also synthesized selectively using the following procedure:

A. Preparation of acetic acid (3S,4R,5S,6S)-2,4,5-triacetoxy-6-[4-chloro-3-(4-ethoxy-benzyl)-phenyl]-tetrahydro-pyran-3-yl ester. The alcohol from Example 1, step D (6.80 g, 12.4 mmol) was treated with 3:2 AcOH/$H_2O$ (62 ml) at 100° C. for 22 hours. The reaction was concentrated under vacuum, rotovapped 3 times with toluene, and placed under high vacuum. The residue was treated with acetic anhydride (9.4 ml, 99.2 mmol) in pyridine (25 ml) for 16 hours. The reaction was quenched with $H_2O$, stirred 1 hour, diluted with $Et_2O$, washed with 1 M aq. $NaHSO_4$, $H_2O$, sat. aq. $NaHCO_3$, and brine (with back extraction), dried over $MgSO_4$, filtered, and concentrated under vacuum. The residue was purified by flash chromatography (120 g SiO$_2$, 0-50% EtOAc/Hex) to give acetic acid (3S,4R,5S,6S)-2,4,5-triacetoxy-6-[4-chloro-3-(4-ethoxy-benzyl)-phenyl]-tetrahydro-pyran-3-yl ester (6.10 g, 10.9 mmol, 87%).

$^1$H NMR (400 MHz, Chloroform-d) δ ppm 7.36 (dd, J=8.08, 2.02 Hz, 1H), 7.19 (dt, J=8.34, 2.02 Hz, 1H), 7.07-7.09 (m, 1H), 7.06 (dd, J=8.72, 1.64 Hz, 2H), 6.83 (d, J=8.59 Hz, 2H), 6.44 (d, J=3.54 Hz, 0.5H α), 5.84 (d, J=8.08 Hz, 0.5H β), 5.55 (t, J=9.98 Hz, 0.5H α), 5.33 (t, J=9.71 Hz, 0.5H β), 5.20-5.27 (m, 1H), 5.09 (t, J=9.60 Hz, 0.5H β), 5.03 (t, J=9.73 Hz, 0.5H α), 4.78 (d, J=10.11 Hz, 0.5H α), 4.47 (d, J=9.85 Hz, 0.5H β), 3.94-4.09 (m, 4H), 2.20 (s, 1.5H α), 2.11 (s, 1.5H β), 2.06 (s, 1.5H β), 2.05 (s, 1.5H α), 2.02 (s, 1.5H α), 2.01 (s, 1.5H β), 1.74 (s, 1.5H α), 1.72 (s, 1.5H β), 1.41 (t, J=6.95 Hz, 3H). MS (ES+) [M+NH$_4$]$^+$=580.

B. Preparation of acetic acid (2S,3S,4R,5S,6S)-4,5-diacetoxy-2-bromo-6-[4-chloro-3-(4-ethoxy-benzyl)-phenyl]-tetrahydro-pyran-3-yl ester. The tetraacetate of step A (8.08 g, 14.4 mmol) was treated with 33% HBr in AcOH (30 ml) for 1 hour. The reaction was diluted with CH$_2$Cl$_2$ (60 ml), stirred for 30 minutes, diluted with more DCM, washed 3× with ice cold H$_2$O and with sat. aq. NaHCO$_3$ (with back extraction), dried over MgSO$_4$, filtered, and concentrated under vacuum to give acetic acid (2S,3S,4R,5S,6S)-4,5-diacetoxy-2-bromo-6-[4-chloro-3-(4-ethoxy-benzyl)-phenyl]-tetrahydro-pyran-3-yl ester.

$^1$H NMR (400 MHz, Chloroform-d) δ ppm 7.37 (d, J=8.34 Hz, 1H), 7.17 (dd, J=8.21, 2.15 Hz, 1H), 7.12 (d, J=2.27 Hz, 1H), 7.06 (d, J=8.59 Hz, 2H), 6.83 (d, J=8.59 Hz, 2H), 6.71 (d, J=4.04 Hz, 1H), 5.64 (t, J=9.73 Hz, 1H), 5.10 (t, J=9.73 Hz, 1H), 4.92-4.98 (m, 2H), 3.94-4.11 (m, 4H), 2.13 (s, 3H), 2.03 (s, 3H), 1.74 (s, 3H), 1.41 (t, J=7.07 Hz, 3H). MS (ES+) [M+NH$_4$]$^+$=602.

C. Preparation of acetic acid (2S,3S,4R,5S,6S)-4,5-diacetoxy-6-[4-chloro-3-(4-ethoxy-benzyl)-phenyl]-2-methoxy-tetrahydro-pyran-3-yl ester. Crude bromide from step B (8.4 g, 14.4 mmol) and ZnO (1.2 g, 14.4 mmol) were dissolved in MeOH (144 ml) and heated at 70° C. for 1 hour. The reaction was cooled to room temperature, filtered through celite with EtOAc, and concentrated under vacuum. The residue was recrystallized from MeOH in two batches to give acetic acid (2S,3S,4R,5S,6S)-4,5-diacetoxy-6-[4-chloro-3-(4-ethoxy-benzyl)-phenyl]-2-methoxy-tetrahydro-pyran-3-yl ester (5.98 g, 11.2 mmol, 78%) as the pure β-anomer.

$^1$H NMR (400 MHz, Chloroform-d) δ ppm 7.37 (d, J=8.08 Hz, 1H), 7.22 (dd, J=8.21, 2.15 Hz, 1H), 7.05-7.10 (m, 3H), 6.80-6.85 (m, 2H), 5.29 (t, J=9.47 Hz, 1H), 5.11 (dd, J=9.73, 7.96 Hz, 1H), 5.02 (t, J=9.73 Hz, 1H), 4.54 (d, J=8.08 Hz, 1H), 4.33 (d, J=9.85 Hz, 1H), 3.96-4.09 (m, 4H), 3.49 (s, 3H), 2.08 (s, 3H), 1.99 (s, 3H), 1.71 (s, 3H), 1.41 (t, J=6.95 Hz, 3H). MS (ES+) [M+NH$_4$]$^+$=552.

D. Preparation of (2S,3R,4R,5S,6S)-2-[4-chloro-3-(4-ethoxy-benzyl)-phenyl]-6-methoxy-tetrahydro-pyran-3,4,5-triol. Recrystallized triacetate from step C (5.98 g, 11.2 mmol) was treated with K$_2$CO$_3$ (7.7 g, 56 mmol) in MeOH (112 ml) with vigorous stirring for 1 hour. The reaction was filtered through celite and concentrated under vacuum. The residue was dissolved in DCM, washed with H$_2$O and brine, dried over MgSO$_4$, filtered, and concentrated under vacuum. The residue was passed through a plug of silica gel with 5% MeOH:CH$_2$Cl$_2$, concentrated under vacuum, suspended in H$_2$O, and lyophilized to give (2S,3R,4R,5S,6S)-2-[4-chloro-3-(4-ethoxy-benzyl)-phenyl]-6-methoxy-tetrahydro-pyran-3,4,5-triol (4.37 g, 10.7 mmol, 96%) as a white solid.

$^1$H NMR (400 MHz, Chloroform-d) δ ppm 7.39 (d, J=8.59 Hz, 1H), 7.23-7.27 (m, 2H), 7.11 (d, J=8.59 Hz, 2H), 6.82 (d, J=8.59 Hz, 2H), 4.33 (d, J=7.83 Hz, 1H), 4.15 (d, J=9.35 Hz, 1H), 3.98-4.12 (m, 4H), 3.68 (t, J=9.09 Hz, 1H), 3.53 (s, 3H), 3.46-3.53 (m, 2H), 2.80 (br. s., 1H), 2.58 (br. s., 1H), 2.09 (br. s., 1H), 1.40 (t, J=7.07 Hz, 3H). MS (ES+) [M+NH$_4$]$^+$=426.

6.6. Example 6

Synthesis of N-[(2S,3S,4R,5R,6S)-6-[4-Chloro-3-(4-ethoxy-benzyl)-phenyl]-3,4,5-trihydroxy-tetrahydro-pyran-2-yl]-N-propyl-acetamide

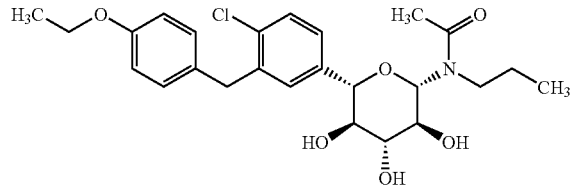

The bromide from Example 5, step B (58 mg, 0.1 mmol) was treated with propylamine (0.1 ml) in CH$_2$Cl$_2$ (0.5 ml) at 40° C. for 1.5 hours. The reaction was blown down with N$_2$, then blown down 2 times from CH$_2$Cl$_2$. The residue was treated with acetic anhydride (78 μl, 0.82 mmol) in pyridine (1 ml) overnight. The reaction was quenched with MeOH, stirred for 30 minutes, diluted with Et$_2$O, washed with 1 M aq. NaHSO$_4$, H$_2$O, sat. aq. NaHCO$_3$, and brine (with back extraction), dried over MgSO$_4$, filtered, and concentrated under vacuum. The intermediate was treated with K$_2$CO$_3$ (14 mg, 0.10 mmol) in MeOH (1 ml) for 1.5 hours. The reaction was filtered and concentrated under vacuum, and the residue was purified by flash chromatography (12 g SiO$_2$, 0-10% MeOH:CH$_2$Cl$_2$) to give 90% pure material. The product was further purified by HPLC (19×50 mm C18 column, 20-70% MeCN:H$_2$O (10 mM NH$_4$OAc), 14 minutes, 30 ml/min), suspended in H$_2$O, and lyophilized to give N-{(2S,3S,4R,5R,6S)-6-[4-chloro-3-(4-ethoxy-benzyl)-phenyl]-3,4,5-trihydroxy-tetrahydro-pyran-2-yl}-N-propyl-acetamide (3 mg, 0.0063 mmol, 15%) as a 2:1 ratio of rotamers.

$^1$H NMR (400 MHz, MeOD) δ ppm 7.29-7.40 (m, 1H), 7.16-7.26 (m, 2H), 7.08 (d, J=8.6 Hz, 2H), 6.81 (d, J=8.6 Hz, 2H), 5.59 (d, J=8.6 Hz, 0.33H), 4.98 (d, J=11.9 Hz, 0.67H), 4.25 (d, J=9.3 Hz, 0.67H), 4.17 (d, J=9.9 Hz, 0.33H), 3.92-4.06 (m, 4H), 3.46-3.64 (m, 3H), 3.06-3.28 (m, 2H), 2.16 (s, 3H), 1.49-1.68 (m, 2H), 1.36 (t, J=6.9 Hz, 3H), 0.93 (t, J=7.5 Hz, 1H), 0.87 (t, J=7.5 Hz, 2H). MS (ES+) [M+H]$^+$=478.

6.7. Example 7

Synthesis of (2R,3S,4S,5S)-5-[4-Chloro-3-(4-ethoxy-benzyl)-phenyl]-2,3,4-tetrahydroxy-pentanal oxime

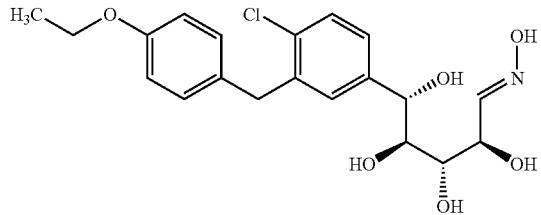

Compound from Example 2 (50 mg, 0.13 mmol) and hydroxylamine hydrochloride (26 mg, 0.38 mmol) were dissolved in pyridine (0.65 ml) and stirred for 3 hours. The reaction was diluted with EtOAc, washed with 1 M aq. NaHSO$_4$, H$_2$O, sat. aq. NaHCO$_3$, and brine (with back extraction), dried over Na$_2$SO$_4$, filtered, and concentrated under vacuum. The residue was suspended in H$_2$O and lyophilized to give (2R,3S,4S,5S)-5-[4-Chloro-3-(4-ethoxy-benzyl)-phenyl]-2,3,4,5-tetrahydroxy-pentanal oxime (46 mg, 0.11 mmol, 88%) as a 5:1 mixture of oxime isomers.

Major isomer $^1$H NMR (400 MHz, MeOD) δ ppm 7.31-7.36 (m, 2H), 7.23-7.30 (m, 2H), 7.10 (d, J=8.8 Hz, 2H), 6.80 (d, J=8.6 Hz, 2H), 4.63 (d, J=8.1 Hz, 1H), 4.28 (t, J=6.8 Hz, 1H), 3.96-4.03 (m, 4H), 3.90-3.94 (m, 1H), 3.59 (dd, J=8.0, 1.6 Hz, 1H), 1.36 (t, J=6.9 Hz, 3H); MS (ES+) [M+H]$^+$=410.

6.8. Example 8

Synthesis of (3S,4R,5R,6S)-6-[4-Chloro-3-(4-ethoxy-benzyl)-phenyl]-3,4,5-trihydroxy-tetrahydro-pyran-2-one oxime

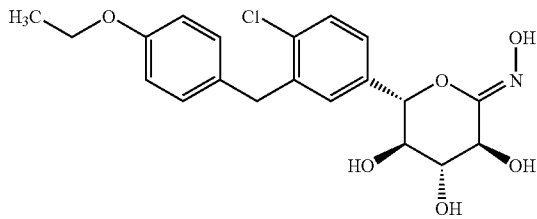

A. Preparation of acetic acid (3S,4R,5S,6S)-4,5-diacetoxy-6-[4-chloro-3-(4-ethoxy-benzyl)-phenyl]-2-hydroxy-tetrahydro-pyran-3-yl ester. The tetraacetate from Example 5, step A (200 mg, 0.36 mmol) was treated with benzylamine (39 µL, 0.36 mmol) in DMF (1.8 ml) for 2 hours. The reaction diluted with Et$_2$O, washed with 1 M aq. NaHSO$_4$, H$_2$O, sat. aq. NaHCO$_3$, and brine, dried over MgSO$_4$, filtered, and concentrated under vacuum. The residue was purified by flash chromatography (12 g SiO$_2$, 0-50% EtOAc:Hex.) to give acetic acid (3S,4R,5S,6S)-4,5-diacetoxy-6-[4-chloro-3-(4-ethoxy-benzyl)-phenyl]-2-hydroxy-tetrahydro-pyran-3-yl ester (142 mg, 0.27 mmol, 77%) as a 3:1 ratio of anomers.

$^1$H NMR (400 MHz, Chloroform-d) δ ppm 7.33-7.40 (m, 1H), 7.18-7.23 (m, 1H), 7.09-7.14 (m, 1H), 7.06 (d, J=8.6 Hz, 2H), 6.82 (d, J=8.6 Hz, 2H), 5.59-5.66 (m, 0.75H), 5.56 (t, J=3.7 Hz, 0.75H), 5.34 (t, J=9.6 Hz, 0.25H), 4.90-5.11 (m, 2.75H), 4.86 (t, J=8.2 Hz, 0.25H), 4.39 (d, J=9.9 Hz, 0.25H), 3.93-4.10 (m, 4H), 3.36 (d, J=8.6 Hz, 0.25H), 2.81 (dd, J=3.8, 1.3 Hz, 0.75H), 2.12 (s, 0.75H), 2.12 (s, 2.25H), 2.02 (s, 0.75H), 2.01 (s, 2.25H), 1.73 (s, 2.25H), 1.72 (s, 0.75H), 1.41 (t, J=7.1 Hz, 3H); MS (ES+) [M+NH$_4$]$^+$=538.

B. Preparation of acetic acid (3S,4R,5S,6S)-4,5-diacetoxy-6-[4-chloro-3-(4-ethoxy-benzyl)-phenyl]-2-[(Z)-hydroxyimino]-tetrahydro-pyran-3-yl ester. Compound from step A (142 mg, 0.27 mmol) and hydroxylamine hydrochloride (57 mg, 0.82 mmol) were dissolved in pyridine (1.4 ml). The reaction was stirred for 6 hours, diluted with EtOAc, washed with 1 M aq. NaHSO$_4$, H$_2$O, sat. aq. NaHCO$_3$, and brine (with back extraction), dried over Na$_2$SO$_4$, filtered, and concentrated under vacuum. The residue was dissolved in CH$_2$Cl$_2$, cooled to −78° C., and treated with DBU (49 µL, 0.33 mmol) followed by N-chlorosuccinimide (44 mg, 0.33 mmol). The reaction was stirred for 20 minutes at −78° C., then allowed to warm to room temperature over 15 minutes The reaction was diluted with EtOAc, washed with H$_2$O and brine (with back extraction), dried over MgSO$_4$, filtered, and concentrated under vacuum. The residue was purified by flash chromatography (12 g SiO$_2$, 0-50% EtOAc:Hex.) to give acetic acid (3S,4R,5S,6S)-4,5-diacetoxy-6-[4-chloro-3-(4-ethoxy-benzyl)-phenyl]-2-[(Z)-hydroxyimino]-tetrahydro-pyran-3-yl ester (97 mg, 0.18 mmol, 67%).

$^1$H NMR (400 MHz, Chloroform-d) δ ppm 7.42 (d, J=8.1 Hz, 1H), 7.30 (dd, J=8.2, 2.1 Hz, 1H), 7.18 (d, J=2.3 Hz, 1H), 7.07 (d, J=8.6 Hz, 2H), 6.83 (d, J=8.6 Hz, 2H), 6.64 (s, 1H), 5.53 (d, J=4.5 Hz, 1H), 5.28 (dd, J=5.8, 4.5 Hz, 1H), 5.16-5.22 (m, 1H), 5.10-5.15 (m, 1H), 3.98-4.10 (m, 4H), 2.19 (s, 3H), 2.07 (s, 3H), 1.78 (s, 3H), 1.41 (t, J=7.1 Hz, 3H); MS (ES+) [M+H]$^+$=534.

C. Preparation of (3S,4R,5R,6S)-6-[4-chloro-3-(4-ethoxy-benzyl)-phenyl]-3,4,5-trihydroxy-tetrahydro-pyran-2-one oxime. Compound from step B (97 mg, 0.18 mmol) was treated with 7.0 M NH$_3$ in MeOH (1.8 ml) for 1 hour. The reaction was concentrated under vacuum, and the residue was purified by flash chromatography (12 g SiO$_2$, 0-12% MeOH:CH$_2$Cl$_2$), suspended in H$_2$O, and lyophilized to give (3S,4R,5R,6S)-6-[4-chloro-3-(4-ethoxy-benzyl)-phenyl]-3,4,5-trihydroxy-tetrahydro-pyran-2-one oxime (57 mg, 0.14 mmol, 77%) as a white solid.

$^1$H NMR (400 MHz, MeOD) δ ppm 7.36-7.44 (m, 2H), 7.31-7.35 (m, 1H), 7.12 (d, J=8.8 Hz, 2H), 6.80 (d, J=8.8 Hz, 2H), 4.91-4.95 (m, 1H), 4.14 (d, J=5.6 Hz, 1H), 4.03-4.10 (m, 2H), 3.99 (q, J=7.1 Hz, 2H), 3.73-3.78 (m, 1H), 3.55 (dd, J=9.9, 6.6 Hz, 1H), 1.36 (t, J=7.1 Hz, 3H); MS (ES+) [M+H]$^+$=408.

6.9. Example 9

Synthesis of (2S,3R,4R,5R)-2-[4-Chloro-3-(4-ethoxy-benzyl)-phenyl]-5-fluoro-6-methoxy-tetrahydro-pyran-3,4-diol

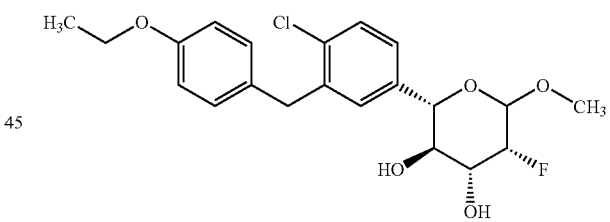

A. Preparation of (2S,3R,4S)-2-(4-chloro-3-(4-ethoxybenzyl)phenyl)-3,4-dihydro-2H-pyran-3,4-diyl diacetate. To a flask charged with 282 mg of tetraacetate from Example 5, step A (0.5 mmol), 1.25 ml of HBr (33% in HOAc) was added. The reaction was stirred for one hour, diluted with 50 ml dichloromethane and quenched by pouring into ice water. The organic layer was separated and washed with saturated aqueous NaHCO$_3$ and brine. After drying over magnesium sulfate, the solvents were concentration in vacuo. The crude residue was taken up in 0.5 ml dichloromethane and added to a suspension of copper(II) sulfate (20 mg, 0.125 mmol), Zn powder (82 mg, 1.25 mmol), and sodium acetate (984 mg, 12 mmol) in 2.5 ml acetic acid/water (3:2 v:v). This mixture was allowed to stir at room temperature for 4 h, after which the reaction was recharged with 20 mg copper(II) sulfate and 82 mg Zn powder and stirred for another 18 h. The mixture was quenched with water, extracted with ethyl acetate. The organic layer was dried over magnesium sulfate and removed in vacuo. Flash chromatography provided (2S,3R,4S)-2-(4-chloro-3-(4-ethoxybenzyl)phenyl)-3,4-dihydro-2H-pyran-3,4-diyl diacetate (32 mg, 16% yield).

$^1$H NMR (400 MHz, Chloroform-d) δ ppm 7.36 (d, J=8.08 Hz, 1H), 7.20 (dd, J=8.08, 2.27 Hz, 1H), 7.16 (d, J=2.27 Hz, 1H), 7.08 (d, J=8.59 Hz, 2H), 6.82 (d, J=8.59 Hz, 2H), 6.57 (dd, J=6.06, 1.52 Hz, 1H), 5.54 (ddd, J=7.07, 2.53, 1.52 Hz, 1H), 5.32 (dd, J=9.60, 7.07 Hz, 1H), 4.83-4.88 (m, 1H), 4.01 (q, J=6.82 Hz, 2H), 3.96-4.10 (m, 2H), 1.96 (s, 3H), 1.77 (s, 3H), 1.40 (t, J=6.82 Hz, 3H). MS (ES+) [M+NH4]+=462.

B. Preparation of (2S,3R,4R,5R,6R)-2-(4-chloro-3-(4-ethoxy-benzyl)-phenyl)-5-fluoro-6-methoxy-tetrahydro-2H-pyran-3,4-diol. Selectfluor™ (45 mg, 0.128 mmol) was added to a solution of compound from step A (38 mg, 0.0853 mmol) in 0.4 mL acetonitrile:methanol (1:1 v:v). The reaction was stirred at ambient temperature and monitored for completion by LCMS. The reaction was quenched with 2 mL saturated aqueous NH4Cl and extracted with diethyl ether (2×5 mL). The organic extracted were dried over sodium sulfate and concentrated in vacuo. Flash chromatography (5 to 10% ethyl acetate/hexanes) provided the fluorinated product. Potassium carbonate (5 mg) was then added to a solution of this isolated product in 0.5 mL of methanol. The reaction was stirred at ambient temperature for 2 h, after which it was quenched with 2 mL water and extracted with ethyl acetate (2×4 mL). The organic layer was filtered over a pad of silica and concentrated to provide 6.3 mg of (2S,3R,4R,5R,6R)-2-(4-chloro-3-(4-ethoxy-benzyl)-phenyl)-5-fluoro-6-methoxy-tetrahydro-2H-pyran-3,4-diol as a clear oil.

$^1$H NMR (400 MHz, Chloroform-d, 3:2 α:β anomeric ratio, 2:1 axial:equatorial fluorine ratio, isomers due to the minor equatorial fluorine structure is noted in italics) δ ppm 7.41 (dd, J=8.34, 2.78 Hz, 1H), 7.20-7.33 (m, 2H), 7.11 (d, J=8.59 Hz, 2H), 6.83 (d, J=8.59 Hz, 2H), 4.92-5.02 (m, 1H), 4.30-4.52 (m, 1H), 3.96-4.27 (m, 6H), 3.74 (t, J=9.09 Hz, 0.66Hα), 3.57*13.56 (s, 3H), 3.49 (t, J=9.09 Hz, 0.33Hβ), 3.42/3.41 (s, 3H). MS (ES+) [M+NH$_4$]$^+$=428.

6.10. Example 10

Synthesis of (2S,3R,4R,5S)-2-[4-Chloro-3-(4-hydroxy-benzyl)-phenyl]-6-methoxy-tetrahydro-pyran-3,4,5-triol

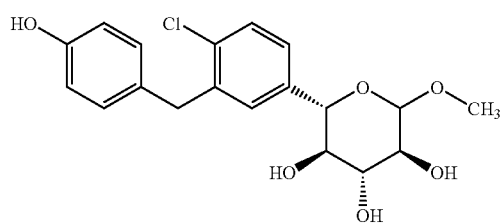

A. Preparation of [4-(5-bromo-2-chloro-benzyl)-phenoxy]-tert-butyl-dimethyl-silane. This compound was prepared as described in U.S. patent application publication no. 2006/0251728 to Himmelsbach et al., published Nov. 9, 2006.

B. (S)-{3-[4-(tert-butyl-dimethyl-silanyloxy)-benzyl]-4-chloro-phenyl}-[(3aS,5S,6R,6aS)-6-(tert-butyl-dimethyl-silanyloxy)-2,2-dimethyl-tetrahydro-furo[2,3-d][1,3]dioxol-5-yl]-methanol. A solution of 0.85 g (2.07 mmol) compound from step A in 4.14 ml diethyl ether was cooled to −78° C.

under an inert atmosphere. To this was added 2.66 ml of tert-butyllithium (1.55 M in hexanes, 4.14 mmol) via syringe over 5 minutes. The reaction was stirred at −78° C. for 30 minutes. A solution of 0.5 g (1.65 mmol) compound from Example 1, step B in 1.65 ml diethyl ether was added. This reaction mixture was stirred at −78° C. for 30 minutes followed by 1.5 h at 0° C. The crude reaction was filtered over a pad of silica gel with excess diethyl ether, which was subsequently removed in vacuo. The product obtained is approximately a 1.2:1 ratio of diastereomers at the newly formed secondary alcohol. The diastereomers were readily separated by chromatography on silica gel (4 to 8% ethyl acetate/hexanes gradient). Yield: 40% (desired diastereomer), 58% (undesired diastereomer).

$^1$H NMR (400 MHz, Chloroform-d) δ ppm 7.17 (d, J=8.34 Hz, 1H), 7.07-7.11 (m, 1H), 7.03 (d, J=1.77 Hz, 1H), 6.85 (d, J=8.59 Hz, 2H), 6.56 (d, J=8.34 Hz, 2H), 5.80 (d, J=3.79 Hz, 1H), 4.70 (d, J=4.80 Hz, 1H), 4.20 (d, J=3.79 Hz, 1H), 4.07 (dd, J=4.80, 3.03 Hz, 1H), 3.97 (d, J=3.03 Hz, 1H), 3.85 (d, J=3.03 Hz, 2H), 3.16 (br. s., 1H), 1.27 (s, 3H), 1.13 (s, 3H), 0.80 (s, 9H), 0.73 (s, 9H), 0.00 (s, 6H), −0.06 (s, 3H), −0.18 (s, 3H).

C. Preparation of (2S,3R,4R,5S)-2-[4-chloro-3-(4-hydroxy-benzyl)-phenyl]-6-methoxy-tetrahydro-pyran-3,4,5-triol. Acetyl chloride (0.17 ml) was added to 7 ml of methanol and stirred for 15 minutes at room temperature. This solution was transferred to a vial charged with 0.446 g compound from step B, which was then sealed and heated to 80° C. for 1 h. The reaction was cooled to ambient temperature and quenched with 50 ml saturated aqueous sodium bicarbonate. This aqueous layer was extracted with ethyl acetate (3×50 ml). The combined organic layers were washed with brine, dried over magnesium sulfate, and the solvent was removed in vacuo. The residue was purified by silica gel chromatography (0 to 20% methanol/dichloromethane gradient) to provide approximately a 1:1 mixture of α:β anomers. Yield: 65%.

$^1$H NMR (400 MHz, Acetone) δ ppm 8.12 (br. s., 1H), 7.33-7.40 (m, 2H), 7.29 (dd, J=8.08, 1.77 Hz, 1H), 7.06 (d, J=8.34 Hz, 3H), 6.75 (d, J=8.34 Hz, 2H), 4.73 (d, J=3.54 Hz, 0.5Hα), 4.41 (d, J=9.60 Hz, 0.5Hα), 4.33 (d, J=7.58 Hz, 0.5Hβ), 4.19 (d, J=9.35 Hz, 0.5Hβ), 4.01 (t, J=3.28 Hz, 2H), 3.72 (t, J=9.09 Hz, 0.5H), 3.44-3.55 (m, 1H), 3.41 (s, 1.5Hβ), 3.35 (s, 1.5Hα), 3.27-3.37 (m, 1.5H). MS (ES+) [M+NH$_4$]$^+$=398.

6.11. Example 11

Synthesis of (2S,3R,4S,5R)-2-[4-Chloro-3-(4-ethoxy-benzyl)-phenyl]-tetrahydro-pyran-3,4,5-triol

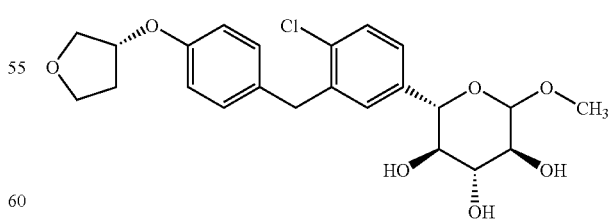

Toluene-4-sulfonic acid (S)-(tetrahydro-furan-3-yl) ester (31 mg, 0.126 mmol) was added to a suspension of compound from Example 10, step C (16 mg, 0.042 mmol) and cesium carbonate (46 mg, 0.126 mmol) in 0.22 ml N,N-dimethylformamide. The reaction vessel was sealed and heated to 80° C.

for 15 h. Upon cooling to room temperature, the crude reaction mixture was quenched with 2 ml brine and extracted with ethyl acetate (3×2 ml). The combined organic extracts were dried over sodium sulfate and concentrated in vacuo. Chromatography on silica gel (0 to 10% methanol/dichloromethane gradient) provided (2S,3R,4S,5R)-2-[4-Chloro-3-(4-ethoxy-benzyl)-phenyl]-tetrahydro-pyran-3,4,5-triol as a clear, viscous oil, which upon concentration in dichloromethane was obtained as a white solid (10 mg, 55% yield).

$^1$H NMR (400 MHz, Acetone) δ ppm 7.35-7.41 (m, 2H), 7.30 (dd, J=8.34, 2.02 Hz, 1H), 7.16 (d, J=7.58 Hz, 2H), 6.83 (d, J=8.59 Hz, 2H), 4.93-5.01 (m, 1H), 4.74 (d, J=3.79 Hz, 0.5Hα), 4.42 (d, J=9.60 Hz, 0.5Hα), 4.33 (d, J=7.58 Hz, 0.5Hβ), 4.20 (d, J=9.60 Hz, 0.5Hβ), 4.05 (t, J=2.53 Hz, 2H), 4.05 (d, J=5.31 Hz, 2H), 3.93 (dd, J=10.11, 4.80 Hz, 1H), 3.75-3.89 (m, 2H), 3.72 (t, J=9.09 Hz, 1H), 3.50 (t, J=9.09 Hz, 1H), 3.41 (s, 1.5Hβ), 3.35 (s, 1.5Hα), 3.29-3.34 (m, 3H), 2.16-2.27 (m, 1H), 1.97-2.04 (m, 1H). MS (ES+) [M+NH4]+=468.

6.12. Example 12

Synthesis of (2S,3S,4S,5R)-2-[4-Chloro-3-(4-hydroxy-benzyl)-phenyl]-piperidine-3,4,5-triol

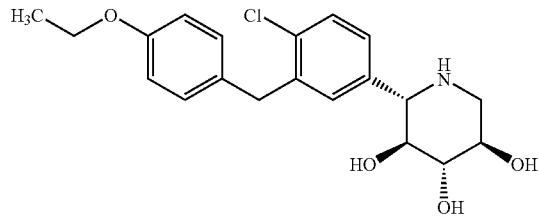

A. Preparation of ((3aS,5S,6R,6aS)-5-{azido-[(S)-4-chloro-3-(4-ethoxy-benzyl)-phenyl]-methyl}-2,2-dimethyl-tetrahydro-furo[2,3-d][1,3]dioxol-6-yloxy)-tert-butyl-dimethyl-silane. To a solution of the C5 epimer of alcohol from Example 1, step D (682 mg, 1.24 mmol) and PPh$_3$ (489 mg, 1.87 mmol) in THF (6.2 ml) was added DIAD (366 μl, 1.87 mmol) followed by diphenyl phosphoryl azide (DPPA, 323 μl, 1.49 mmol). The reaction was stirred for 1.5 hours, quenched with sat. aq. NH$_4$Cl, diluted with Et$_2$O, washed with H$_2$O and brine (with back extraction), dried over MgSO$_4$, and concentrated under vacuum. The residue was purified by flash chromatography (40 g SiO$_2$, 0-8% EtOAc:Hex.) to give ((3aS,5S,6R,6aS)-5-{azido-[(S)-4-chloro-3-(4-ethoxy-benzyl)-phenyl]-methyl}-2,2-dimethyl-tetrahydro-furo[2,3-d][1,3]dioxol-6-yloxy)-tert-butyl-dimethyl-silane (636 mg, 1.11 mmol, 89%) as a yellow oil.

$^1$H NMR (400 MHz, Chloroform-d) δ ppm 7.40 (d, J=8.08 Hz, 1H), 7.16-7.20 (m, 1H), 7.15 (d, J=2.02 Hz, 1H), 7.10 (d, J=8.59 Hz, 2H), 6.80-6.85 (m, 2H), 5.79 (d, J=3.54 Hz, 1H), 4.58 (d, J=9.85 Hz, 1H), 4.36 (d, J=3.54 Hz, 1H), 4.30 (d, J=2.53 Hz, 1H), 4.14 (dd, J=9.98, 2.65 Hz, 1H), 3.98-4.10 (m, 4H), 1.38-1.43 (m, 6H), 1.29 (s, 3H), 0.96 (s, 9H), 0.20 (s, 6H); MS (ES+) [M+NH$_4$]$^+$=591.

B. Preparation of (2R,3S,455 S)-5-{azido-[(S)-4-chloro-3-(4-ethoxy-benzyl)-phenyl]-methyl}-tetrahydro-furan-2,3,4-triol. Acetyl chloride (0.175 ml, 2.45 mmol) was added to MeOH (7 ml). The solution was stirred 15 minutes, then added to azide from step A (392 mg, 0.68 mmol). The reaction was stirred for 16 hours, then concentrated under vacuum, rotovapped 2 times with MeOH, and placed on the high vacuum to give a white solid. The solid was treated with 1:1 AcOH:H$_2$O (7 ml) at 100° C. for 2.5 hours. The reaction was concentrated under vacuum, rotovapped 2 times with toluene, and placed on the high vacuum. The residue was purified by flash chromatography (40 g SiO$_2$, 0-6% MeOH:CH$_2$Cl$_2$) to give (2R,3S,4S,5S)-5-{azido-[(S)-4-chloro-3-(4-ethoxy-benzyl)-phenyl]-methyl}-tetrahydro-furan-2,3,4-triol (223 mg, 0.53 mmol, 78%) as a mixture of anomers.

$^1$H NMR (400 MHz, MeOD) δ ppm 7.39 (dd, J=8.46, 3.41 Hz, 1H), 7.24-7.30 (m, 2H), 7.09 (d, J=8.84 Hz, 2H), 6.81 (dd, J=8.59, 1.77 Hz, 2H), 5.33 (d, J=3.54 Hz, 0.5H), 4.98 (s, 0.5H), 4.84 (d, J=10.17 Hz, 0.5H), 4.66 (d, J=9.09 Hz, 0.5H), 4.10-4.23 (m, 2H), 3.97-4.05 (m, 4.5H), 3.89 (dd, J=3.66, 1.89 Hz, 0.5H), 1.36 (t, J=6.95 Hz, 3H); MS (ES+) [M+NH$_4$]$^+$=437.

C. Preparation of (2S,3S,4S,5R)-2-[4-chloro-3-(4-ethoxy-benzyl)-phenyl]-piperidine-3,4,5-triol. Compound from step B (216 mg, 0.52 mmol) was hydrogenated under atmospheric pressure H$_2$ over PtO$_2$ (6 mg, 0.026 mmol) in MeOH (5 ml) with AcOH (0.25 ml) for 6 hours. The reaction was filtered, concentrated under vacuum, diluted with EtOAc, washed with 10% aq. K$_2$CO$_3$ and brine, dried over Na$_2$SO$_4$, filtered, and concentrated under vacuum. A portion of the material (about 55 mg) was purified prep HPLC (Sunfire C18 30×100 mm column, 20-70% MeCN:H$_2$O (10 mM NH$_4$OAc), 15 minutes, 45 ml/min) and lyophilized to give (2S,3S,4S,5R)-2-[4-chloro-3-(4-ethoxy-benzyl)-phenyl]-piperidine-3,4,5-triol (27 mg, 0.071 mmol) as a white solid.

$^1$H NMR (400 MHz, MeOD) δ ppm 7.35 (d, J=8.08 Hz, 1H), 7.29 (d, J=2.02 Hz, 1H), 7.21-7.25 (m, 1H), 7.10 (d, J=8.34 Hz, 2H), 6.79 (d, J=8.59 Hz, 2H), 4.02 (s, 2H), 3.99 (q, J=7.07 Hz, 2H), 3.57 (ddd, J=10.55, 8.65, 5.05 Hz, 1H), 3.33-3.40 (m, 2H), 3.25-3.29 (m, 1H), 3.12 (dd, J=12.00, 5.18 Hz, 1H), 2.56 (dd, J=11.87, 10.86 Hz, 1H), 1.35 (t, J=6.95 Hz, 3H); MS (ES+) [M+H]$^+$=378.

6.13. Example 13

Synthesis of (2S,3R,4R,5S,6R)-2-[4-Chloro-3-(4-ethanesulfinyl-tetrahydro-pyran-3,4,5-triol and (2S,3R,4R,5S,6R)-2-[4-Chloro-3-(4-ethoxy-benzyl)-phenyl]-6-ethanesulfonyl-tetrahydro-pyran-3,4,5-triol

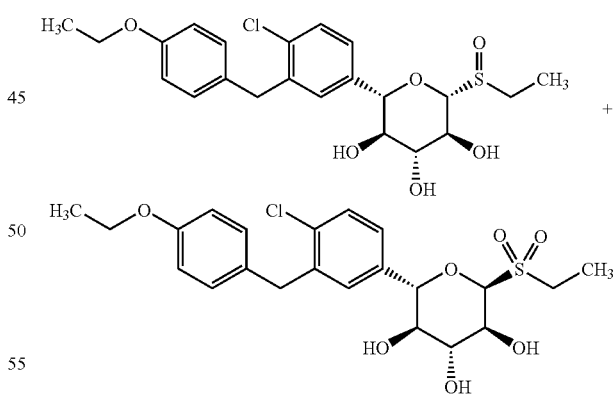

A. Preparation of (2S,3R,4R,5S,6R)-2-[4-chloro-3-(4-ethoxy-benzyl)-phenyl]-6-ethylsulfanyl-tetrahydro-pyran-3,4,5-triol. To a solution of bromide from Example 5, step B (291 mg, 0.50 mmol) in EtOH (5 ml) at 0° C. was added NaSEt (84 mg, 1.0 mmol). The reaction was stirred 30 minutes, then diluted with EtOAc, washed with dilute aq. NaOH and with brine (with back extraction), dried over Na$_2$SO$_4$, filtered, and concentrated under vacuum. The residue was purified by flash chromatography (40 g SiO$_2$, 0-7% MeOH:CH$_2$Cl$_2$), suspended in H$_2$O, and lyophilized to give (2S,3R, 4R,5S,6R)-2-[4-chloro-3-(4-ethoxy-benzyl)-phenyl]-6-ethylsulfanyl-tetrahydro-pyran-3,4,5-triol (126 mg, 0.29 mmol, 58%) as a white powder.

$^1$H NMR (400 MHz, Chloroform-d) δ ppm 7.39 (d, J=8.08 Hz, 1H), 7.18-7.26 (m, 2H), 7.10 (d, J=8.59 Hz, 2H), 6.80-6.85 (m, 2H), 4.46 (d, J=9.60 Hz, 1H), 4.17 (d, J=9.35 Hz, 1H), 3.98-4.11 (m, 4H), 3.67-3.73 (m, 1H), 3.49-3.57 (m, 2H), 2.79 (d, J=2.27 Hz, 1H), 2.67-2.77 (m, 2H), 2.53 (d, J=1.77 Hz, 1H), 2.04 (d, J=2.78 Hz, 1H), 1.41 (t, J=6.95 Hz, 3H), 1.29 (t, J=7.45 Hz, 3H); MS (ES+) [M+NH$_4$]$^+$=456.

B. Preparation of (2S,3R,4R,5S,6R)-2-[4-chloro-3-(4-ethoxy-benzyl)-phenyl]-6-ethanesulfinyl-tetrahydro-pyran-3,4,5-triol and (2S,3R,4R,5S,6R)-2-[4-Chloro-3-(4-ethoxy-benzyl)-phenyl]-6-ethanesulfonyl-tetrahydro-pyran-3,4,5-triol. To a solution of compound from step A (10 mg, 0.023 mmol) in AcOH (0.5 ml) was added H$_2$O$_2$ (35 wt % solution in H$_2$O, 3 mg, 0.092 mmol, 9 μl). The mixture was stirred at ambient temperature for 2 hours before being concentrated under vacuum. Purification of the mixture by silica gel chromatography (5% MeOH/CH$_2$Cl$_2$) afforded (2S,3R,4R,5S,6R)-2-[4-chloro-3-(4-ethoxy-benzyl)-phenyl]-6-ethanesulfinyl-tetrahydro-pyran-3,4,5-triol (as a mixture of diastereomers at sulfur) (2 mg, 19%) and (2S,3R,4R,5S,6R)-2-[4-Chloro-3-(4-ethoxy-benzyl)-phenyl]-6-ethanesulfonyl-tetrahydro-pyran-3,4,5-triol (5 mg, 46%) both as white solids.

(2S,3R,4R,5S,6R)-2-[4-chloro-3-(4-ethoxy-benzyl)-phenyl]-6-ethanesulfinyl-tetrahydro-pyran-3,4,5-triol: $^1$H NMR (400 MHz, methanol) δ ppm 7.37 (m, 3H), 7.31 (m, 1H), 7.24 (m, 2H), 7.10 (m, 4H) 6.81 (m, 4H), 4.46 (d, J=9.9 Hz, 1H), 4.28 (d, J=9.6 Hz, 1H), 4.25 (d, J=9.6 Hz, 1H), 4.19 (d, J=9.9 Hz, 1H), 4.03 (m, 4H), 4.00 (m, 4H), 3.85 (t, J=9.6 Hz, 1H), 3.76 (t, J=9.6 Hz, 1H), 3.57 (m, 2H), 3.37 (m, 2H), 3.09 (m, 1H), 2.99 (m, 1H), 2.91 (m, 1H), 2.80 (m, 1H), 1.31 (m, 12H); MS (ES+) [M+H]$^+$=455.

(2S,3R,4R,5S,6R)-2-[4-chloro-3-(4-ethoxy-benzyl)-phenyl]-6-ethanesulfonyl-tetrahydro-pyran-3,4,5-triol: $^1$H NMR (400 MHz, methanol) δ ppm 7.28 (m, 1H), 7.16 (m, 2H), 6.99 (d, J=8.6 Hz, 2H), 6.71 (d, J=8.6 Hz, 2H), 4.46 (d, J=9.6 Hz, 1H), 4.19 (d, J=9.4 Hz, 1H), 3.90 (m, 4H), 3.81 (t, J=9.3 Hz, 1H), 3.46 (t, J=9.1 Hz, 1H), 3.24 (t, J=9.1 Hz, 1H), 2.98 (m, 2H), 1.26 (t, J=6.8 Hz, 3H), 1.18 (t, J=7.6 Hz, 3H); MS (ES+) [M+NH$_4$]$^+$=488.

6.14. Example 14

Synthesis of Acetic acid (2R,3S,4R,5S,6S)-4,5-diacetoxy-6-[4-chloro-3-(4 ethoxy-benzyl)-phenyl]-2-methylsulfanyl-tetrahydro-pyran-3-yl ester

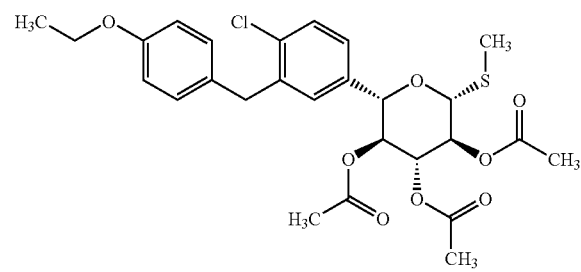

A. Preparation of (2S,3R,4R,5S,6R)-2-[4-chloro-3-(4-ethoxy-benzyl)-phenyl]-6-methylsulfanyl-tetrahydro-pyran-3,4,5-triol. To a solution of bromide from Example 5, step B (347 mg, 0.60 mmol.) in EtOH (6 ml) at 0° C. was added NaSMe (70 mg, 0.72 mmol.). The reaction was stirred 30 minutes, then diluted with EtOAc, washed with dilute aq. NaOH and with brine (with back extraction), dried over Na$_2$SO$_4$, filtered, and concentrated under vacuum. The residue was purified by flash chromatography (40 g SiO$_2$, 0-7% MeOH:CH$_2$Cl$_2$), suspended in H$_2$O, and lyophilized to give (2S,3R,4R,5S,6R)-2-[4-chloro-3-(4-ethoxy-benzyl)-phenyl]-6-methylsulfanyl-tetrahydro-pyran-3,4,5-triol (212 mg, 0.43 mmol., 72%) as a white powder.

$^1$H NMR (400 MHz, Chloroform-d) δ ppm 7.39 (d, J=8.34 Hz, 1H), 7.22 (dd, J=8.08, 2.27 Hz, 1H), 7.17 (d, J=2.02 Hz, 1H), 7.10 (d, J=8.59 Hz, 2H), 6.83 (d, J=8.84 Hz, 2H), 4.38 (d, J=9.60 Hz, 1H), 4.19 (d, J=9.35 Hz, 1H), 3.98-4.11 (m, 4H), 3.67-3.73 (m, 1H), 3.48-3.59 (m, 2H), 2.80 (d, J=2.27 Hz, 1H), 2.53 (d, J=2.02 Hz, 1H), 2.19 (s, 3H), 2.04 (d, J=2.78 Hz, 1H), 1.41 (t, J=6.95 Hz, 3H); MS (ES+) [M+NH$_4$]$^+$=442.

B. Preparation of acetic acid (2R,3S,4R,5S,6S)-4,5-diacetoxy-6-[4-chloro-3-(4-ethoxy-benzyl)-phenyl]-2-methylsulfanyl-tetrahydro-pyran-3-yl ester. Triol from step A (45 mg, 0.11 mmol.) was treated with acetic anhydride (60 μl, 0.64 mmol.) in pyridine (0.5 ml) for 16 hours. The reaction was diluted with Et$_2$O, washed with 1 M aq. NaHSO$_4$, H$_2$O, sat. aq. NaHCO$_3$, and brine (with back extraction), dried over MgSO$_4$, filtered, and concentrated under vacuum. The residue was purified by flash chromatography (4 g SiO$_2$, 0-25% EtOAc/Hex), suspended in H$_2$O, and lyophilized to acetic acid (2R,3S,4R,5S,6S)-4,5-diacetoxy-6-[4-chloro-3-(4-ethoxy-benzyl)-phenyl]-2-methylsulfanyl-tetrahydro-pyran-3-yl ester (46 mg, 0.087 mmol., 79%) as a white solid.

$^1$H NMR (400 MHz, Chloroform-d) δ ppm 7.36 (d, J=8.08 Hz, 1H), 7.18 (dd, J=8.21, 2.15 Hz, 1H), 7.02-7.10 (m, 3H), 6.83 (d, J=8.59 Hz, 2H), 5.27-5.34 (m, 1H), 5.19 (t, J=9.60 Hz, 1H), 5.04 (t, J=9.60 Hz, 1H), 4.50 (d, J=9.85 Hz, 1H), 4.37 (d, J=9.85 Hz, 1H), 3.95-4.08 (m, 4H), 2.16 (s, 3H), 2.10 (s, 3H), 2.00 (s, 3H), 1.72 (s, 3H), 1.41 (t, J=7.07 Hz, 3H); MS (ES+) [M+NH$_4$]$^+$=568.

6.15. Example 15

Synthesis of (2S,3R,4R,5S,6R)-2-[4-Chloro-3-(4-ethoxy-benzyl)-phenyl]-6-methanesulfonyl-tetrahydro-pyran-3,4,5-triol

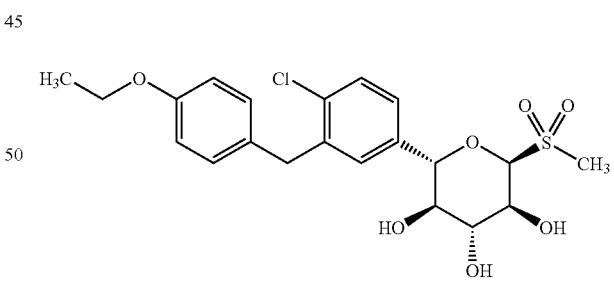

To a solution of the compound from Example 14, step A (41 mg, 0.097 mmol) in AcOH (0.5 ml) was added H$_2$O$_2$ (35 wt % solution in H$_2$O, 20 mg, 0.58 mmol, 57 μl). The mixture was stirred at ambient temperature for 18 hours before being concentrated under vacuum. Purification of the mixture by silica gel chromatography (5% MeOH/CH$_2$Cl$_2$) afforded (2S,3R,4R,5S,6R)-2-[4-chloro-3-(4-ethoxy-benzyl)-phenyl]-6-methanesulfonyl-tetrahydro-pyran-3,4,5-triol (20 mg, 45%) as a white solid.

$^1$H NMR (400 MHz, methanol) δ ppm 7.28 (m, 1H), 7.27 (m, 2H), 7.10 (d, J=8.4 Hz, 2H), 6.81 (d, J=8.4 Hz, 2H), 4.53

(d, J=9.6 Hz, 1H), 4.30 (d, J=9.6 Hz, 1H), 4.00 (m, 4H), 3.88 (t, J=9.1 Hz, 1H), 3.55 (t, J=9.1 Hz, 1H), 3.35 (t, J=9.1 Hz, 1H), 2.92 (s, 3H), 1.36 (t, J=6.8 Hz, 3H); MS (ES+) [M+NH$_4$]$^+$=474.

6.16. Example 16

Synthesis of 1-[(2S,3S,4S,5R)-2-[4-Chloro-3-(4-ethoxy-benzyl)-phenyl]-3,4,5-trihydroxy-piperidin-1-yl]-ethanone

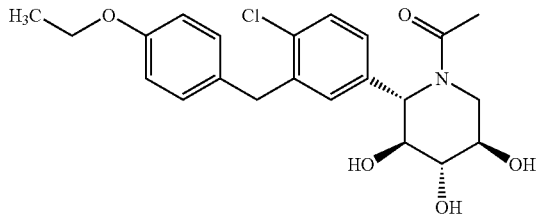

Preparation of 1-{(2S,3S,4S,5R)-2-[4-chloro-3-(4-ethoxy-benzyl)-phenyl]-3,4,5-trihydroxy-piperidin-1-yl}-ethanone. To a solution of the crude compound from Example 12, step C (38 mg, 0.1 mmol.) in MeOH (1 mL) was added acetic anhydride (19 µL, 0.2 mmol.). The reaction was stirred for 4 hours, more acetic anhydride (10 µL, 0.1 mmol) was added, and stirring was continued overnight. The reaction was diluted with EtOAc, washed with sat. aq. NaHCO$_3$ and brine, dried over Na$_2$SO$_4$, filtered, and concentrated under vacuum. The residue was purified by flash chromatography (12 g SiO$_2$, 0-8% MeOH:CH$_2$Cl$_2$), suspended in H$_2$O, and lyophilized to give 1-{(2S,3S,4S,5R)-2-[4-chloro-3-(4-ethoxy-benzyl)-phenyl]-3,4,5-trihydroxy-piperidin-1-yl}-ethanone (14 mg, 0.033 mmol., 33% for 2 steps) as a white solid.

$^1$H NMR (400 MHz, MeOD) δ ppm 7.33 (d, J=8.34 Hz, 1H), 7.18 (dd, J=8.46, 2.15 Hz, 1H), 7.11 (d, J=1.77 Hz, 1H), 7.07 (d, J=8.84 Hz, 2H), 6.81 (d, J=8.84 Hz, 2H), 3.96-4.03 (m, 4H), 3.83-3.89 (m, 1H), 3.73-3.77 (m, 1H), 3.55-3.59 (m, 1H), 2.09 (br. s., 3H), 1.36 (t, J=6.95 Hz, 3H); MS (ES+) [M+H]$^+$=420.

6.17. Example 17

Synthesis of (2S,3S,4S,5R)-2-[4-Chloro-3-(4-ethoxy-benzyl)-phenyl]-3,4,5-trihydroxy-piperidine-1-carboxylic acid methyl ester

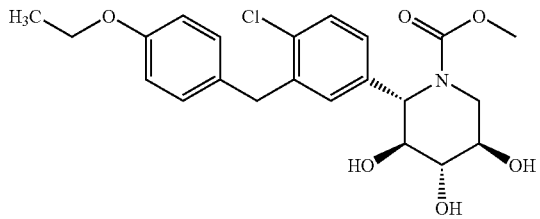

To a solution of the crude compound from Example 12, step C (38 mg, 0.1 mmol.) and NaHCO$_3$ (42 mg, 0.5 mmol.) in 1:1:1 EtOAc:EtOH:H$_2$O (1.5 mL) at 0° C. was added methyl chloroformate (23 µL, 0.3 mmol.). The reaction was stirred for 1 hour, then diluted with EtOAc, washed with H$_2$O and brine (with back extraction), dried over Na$_2$SO$_4$, filtered, and concentrated under vacuum. The residue was purified by flash chromatography (4 g SiO$_2$, 0-10% MeOH:CH$_2$Cl$_2$, suspended in H$_2$O, and lyophilized to give (2S,3S,4S,5R)-2-[4-chloro-3-(4-ethoxy-benzyl)-phenyl]-3,4,5-trihydroxy-piperidine-1-carboxylic acid methyl ester (12 mg, 0.026 mmol., 26% for 2 steps) as a white solid.

$^1$H NMR (400 MHz, MeOD) δ ppm 7.32 (d, J=8.34 Hz, 1H), 7.15 (dd, J=8.34, 2.02 Hz, 1H), 7.10 (d, J=2.27 Hz, 1H), 7.04-7.09 (m, 2H), 6.81 (d, J=8.59 Hz, 2H), 4.80 (d, J=6.06 Hz, 1H), 4.00 (q, J=7.07 Hz, 5H), 3.81-3.86 (m, 1H), 3.70-3.73 (m, 1H), 3.60 (s, 3H), 3.54-3.59 (m, 1H), 3.46 (dd, J=14.40, 3.28 Hz, 1H), 1.36 (t, J=6.95 Hz, 3H); MS (ES+) [M+H]$^+$=436.

6.18. Example 18

Synthesis of (2S,3S,4S,5R)-2-[4-Chloro-3-(4-ethoxy-benzyl)-phenyl]-3,4,5-trihydroxy-piperidine-1-carboxylic acid allyl amide

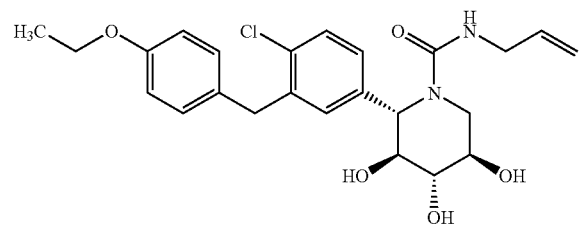

To a solution of the crude compound from Example 12, step C (38 mg, 0.1 mmol.) in 1:1 EtOH:EtOAc (1 mL) was added allyl isocyanate (18 µL, 0.2 mmol.). The reaction was stirred for 1 hour, then concentrated under vacuum. The residue was purified by flash chromatography (4 g SiO$_2$, 0-10% MeOH:CH$_2$Cl$_2$, suspended in H$_2$O, and lyophilized to give (2S,3S,4S,5R)-2-[4-chloro-3-(4-ethoxy-benzyl)-phenyl]-3,4,5-trihydroxy-piperidine-1-carboxylic acid allyl amide (14 mg, 0.030 mmol., 30% for 2 steps) as a white solid.

$^1$H NMR (400 MHz, MeOD) δ ppm 7.32 (d, J=8.1 Hz, 1H), 7.16-7.20 (m, 2H), 7.07 (d, J=8.8 Hz, 2H), 6.80 (d, J=8.8 Hz, 2H), 5.68-5.79 (m, J=17.2, 10.2, 5.3, 5.2 Hz, 1H), 4.92-5.00 (m, 2H), 4.77 (d, J=6.3 Hz, 1H), 3.94-4.05 (m, 4H), 3.86 (dd, J=14.0, 3.4 Hz, 1H), 3.69-3.81 (m, 3H), 3.59-3.68 (m, 1H), 3.56 (dd, J=7.3, 5.1 Hz, 1H), 3.47 (dd, J=13.9, 3.5 Hz, 1H), 1.36 (t, J=6.9 Hz, 3H); MS (ES+) [M+H]$^+$=461.

6.19. Example 19

Synthesis of (2S,3S,4S,5R)-2-[4-Chloro-3-(4-ethoxy-benzyl)-phenyl]-1-methyl-piperidine-3,4,5-triol

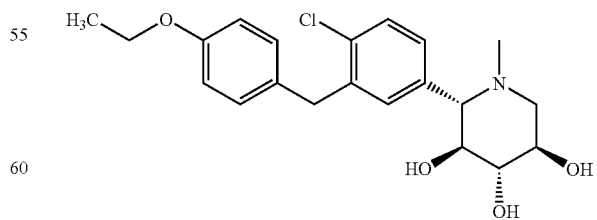

To a solution of the compound from Example 12, step C (50 mg, 0.13 mmol.) and K$_2$CO$_3$ (55 mg, 0.40 mmol.) in DMF (0.65 mL) was added methyl iodide (10 µL, 0.16 mmol.). The reaction was stirred for 3 hours, then diluted with EtOAc, washed with H₂O and brine (with back extraction), dried over Na₂SO₄, filtered, and concentrated under vacuum. The residue was purified by flash chromatography (12 g SiO₂, 2-12% MeOH:CH₂Cl₂), suspended in H₂O, and lyophilized to give (2S,3S,4S,5R)-2-[4-chloro-3-(4-ethoxy-benzyl)-phenyl]-1-methyl-piperidine-3,4,5-triol (16 mg, 0.040 mmol., 31%) as a white solid.

$^1$H NMR (400 MHz, MeOD) δ ppm 7.35 (d, J=8.1 Hz, 1H), 7.20-7.24 (m, 1H), 7.17 (dd, J=8.2, 1.9 Hz, 1H), 7.09 (d, J=8.6 Hz, 2H), 6.80 (d, J=8.6 Hz, 2H), 4.03 (s, 2H), 3.99 (q, J=7.1 Hz, 2H), 3.64 (ddd, J=10.5, 9.2, 4.8 Hz, 1H), 3.33-3.37 (m, 1H), 3.21 (t, J=9.0 Hz, 1H), 3.03 (dd, J=11.1, 4.8 Hz, 1H), 2.74 (d, J=9.3 Hz, 1H), 2.15 (t, J=10.9 Hz, 1H), 1.95 (s, 3H), 1.36 (t, J=6.9 Hz, 3H); MS (ES+) [M+H]$^+$=392.

6.20. Example 20

Synthesis of (2S,3S,4R,5R,6R)-2-[3-(4-Ethoxy-benzyl)-phenyl]-6-hydroxymethyl-1-methyl-piperidine-3,4,5-triol

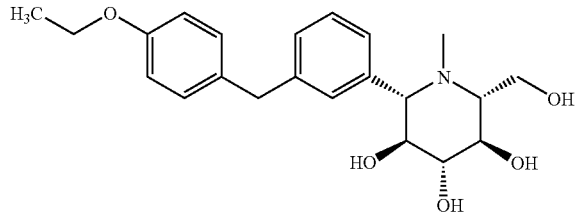

A. Preparation of (3R,4S,5R,6R)-3,4,5-tris(benzyloxy)-6-(benzyloxymethyl) tetrahydro-2H-pyron-2-one. Tetra-O-benzyl-D-glucopyranose (2.07 g, 3.8 mmol) was dissolved in DMSO (10.1 mL). To this mixture was added acetic anhydride (7.0 mL) and stirred at room temperature overnight. To the reaction mixture ice was added and stirred for 1 h. The mixture was extracted with ether (3×20 mL). The extract was washed with water (2×10 mL), aqueous sodium bicarbonate (2×10 mL), brine, dried (sodium sulfate) and concentrated under vacuo. Flash silica gel column chromatography with 0-25% ethylacetate/Hexane resulted in 1.712 g of (3R,4S,5R,6R)-3,4,5-tris(benzyloxy)-6-(benzyloxymethyl) tetrahydro-2H-pyron-2-one (83%).

B. Preparation of (3R,4S,5R,6R)-3,4,5-tris(benzyloxy)-6-(benzyloxymethyl)-2-(4-chloro-3-(4-ethoxybenzyl)phenyl) tetrahydro-2H-pyran-2-ol. n-Butyl lithium (2.5N in hexane) (1.263 mL, 3.16 mmol) was added dropwise to a solution of compound from Example 1, step C (1.028 g, 3.16 mmol) in anhydrous THF (15 mL) at −78° C. After stirring for 30 min at −78° C., a solution of compound from step A (1.7 g, 3.16 mmol) in anhydrous THF (10 mL) was added dropwise and stirred for 1 h while allowing to warm to room temperature. Aqueous ammonium chloride (10 mL) was added to the reaction mixture, THF removed under vacuum, and aqueous layer extracted with ethyl acetate (2×20 mL). Combined organic phases washed with brine, dried (sodium sulfate) and concentrated under vacuum. Crude mixture purified by flash silica gel column chromatography with 0-20% ethyl acetate/Hexane to give 712 mg of (3R,4S,5R,6R)-3,4,5-tris(benzyloxy)-6-(benzyloxymethyl)-2-(4-chloro-3-(4-ethoxybenzyl)phenyl)tetrahydro-2H-pyran-2-ol (29%). M+H₂O=802.1

C. Preparation of (2R,3R,4S)-2,3,4,6-tetrakis(benzyloxy)-1-(4-chloro-3-(4-ethoxybenzyl)phenyl)hexane-1,5-dione. To a stirred solution of Dess-Martin reagent (500 mg, excess) in CH₂Cl₂ (10 mL) was added compound from step B (500 mg, 0.6 mmol)) in anhydrous dichloromethane (10 mL) and stirred overnight. Reaction mixture quenched with 1N sodium hydroxide (3 mL), extracted with dichloromethane (2×10 mL), combined organic fractions were washed with brine, dried over sodium sulfate, concentrated under reduced pressure to get crude product 487 mg. (M+H₂O=800.1)

D. Preparation of (3R,4R,5S)-3,4,5-tris(benzyloxy)-2-(benzyloxymethyl)-6-(4-chloro-3-(4-ethoxybenzyl)phenyl) piperidine. A solution of compound from step C (400 mg, 0.5 mmol), 7N ammonia in MeOH (1.0 mL) and freshly activated 4 Å molecular sieves (250 mg) in dichloromethane (20 mL) were refluxed overnight. The reaction mixture was cooled to room temperature, then sodium cyanoborohydride (160 mg, 2.55 mmol) was added and refluxed for additional 2 h. The reaction mixture was filtered, diluted with dichloromethane (20 mL), washed with water, brine, dried (sodium sulfate), and concentrated under reduced pressure. Chromatography on silica gel (50 to 100% acetonitrile containing 0.1% ammonium acetate/water gradient) provided (3R,4R,5S)-3,4,5-tris(benzyloxy)-2-(benzyloxymethyl)-6-(4-chloro-3-(4-ethoxybenzyl)phenyl)piperidine (136 mg, 34%).

$^1$H NMR (400 MHz, Chloroform-d) δ ppm 1.41 (t, J=7.07 Hz, 3H) 2.98 (ddd, J=9.40, 8.50, 2.53 Hz, 1H) 3.40 (t, J=9.22 Hz, 1H) 3.41 (t, J=8.59 Hz, 1H) 3.43 (t, J=9.09 Hz, 1H) 3.56 (d, J=9.35 Hz, 1H) 3.68 (t, J=8.84 Hz, 1H) 3.79 (dd, J=8.97, 2.65 Hz, 1H) 3.84 (d, J=10.36 Hz, 1H) 3.97 (d, J=13.60 Hz, 1H) 3.99 (q, J=7.07 Hz, 2H) 4.10 (d, J=15.30 Hz, 1H) 4.43 (d, J=10.36 Hz, 1H) 4.48 (d, J=2.53 Hz, 2H) 4.56 (d, J=10.86 Hz, 1H) 4.88 (d, J=10.86 Hz, 1H) 4.89 (d, J=11.12 Hz, 1H) 4.93 (d, J=10.86 Hz, 1H) 6.77 (d, J=8.59 Hz, 2H) 6.88 (dd, J=7.71, 1.64 Hz, 2H) 7.07 (d, J=8.59 Hz, 2H) 7.16-7.38 (m, 21H); MS (ES+) [M+H]$^+$=768.2.

E. Preparation of (3R,4R,5S)-3,4,5-tris(benzyloxy)-2-(benzyloxymethyl)-6-(4-chloro-3-(4-ethoxybenzyl)phenyl)-1-methylpiperidine. Compound from step D (50 mg, 0.065 mmol) was dissolved in acetonitrile (1 mL) and treated with potassium carbonate (18 mg, 0.13 mmol) for 30 minutes To this mixture iodomethane (20 uL, 0.32 mmol) was added and stirred overnight. The reaction mixture was diluted with ethyl acetate (10 mL), washed with water, brine, dried (sodium sulfate), and concentrated under vacuum. Chromatography on silica gel (50 to 100% acetonitrile containing 0.1% ammonium acetate/water gradient) provided (3R,4R,5S)-3,4,5-tris(benzyloxy)-2-(benzyloxymethyl)-6-(4-chloro-3-(4-ethoxybenzyl)phenyl)-1-methylpiperidine (29 mg, 56%). MH+782.1.

F. Preparation of (2S,3S,4R,5R,6R)-2-[3-(4-ethoxy-benzyl)-phenyl]-6-hydroxymethyl-1-methyl-piperidine-3,4,5-triol. Compound from step E (50 mg) in methanol and acetic acid (25 uL) was treated 5% wet Pd—C (10 mg) under H₂ atmosphere for 4 h. The reaction mixture was filtered through a pad of celite and concentrated. Chromatography on silica gel (10 to 100% acetonitrile containing 0.1% ammonium acetate/water gradient) provided (2S,3S,4R,5R,6R)-2-[3-(4-ethoxy-benzyl)-phenyl]-6-hydroxymethyl-1-methyl-piperidine-3,4,5-triol (6 mg, 70%).

$^1$H NMR (400 MHz, Chloroform-d) δ ppm 1.40 (t, J=6.95 Hz, 3H) 2.02 (s, 3H) 2.05 (br. s., 3H) 2.15 (d, J=8.84 Hz, 1H) 3.01 (d, J=4.55 Hz, 2H) 3.50 (d, J=5.05 Hz, 2H) 3.77 (br. s., 2H) 3.85 (d, J=8.59 Hz, 2H) 3.91 (br. s., 2H) 3.99 (q, J=7.24

Hz, 2H) 6.81 (d, J=8.59 Hz, 2H) 7.06 (d, J=8.59 Hz, 2H) 7.09 (br. s., 1H) 7.18 (br. s., 2H) 7.24 (d, J=7.58 Hz, 1H); MS (ES+) [M+H]$^+$=387.0.

6.21. Example 21

Synthesis of (2S,3R,4R,5S,6R)-2-(4-chloro-3-(4-ethoxybenzyl)phenyl)-6-methoxytetrahydro-2H-thiopyran-3,4,5-triol

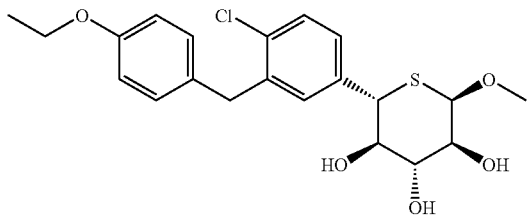

A. Preparation of (S-(1S)-((3aS,6S,6aS)-6-(tert-butyldimethylsilyloxy)-2,2-dimethyltetrahydrofuro[2,3-d][1,3]dioxol-5-yl)(4-chloro-3-(4-ethoxybenzyl)phenyl)methyl benzothioate. Diethylazodicarboxylate (150 µL, 0.914 mmol) was added to a solution of triphenylphosphine (240 mg, 0.914 mmol) in 1.0 mL of THF at room temperature. After one hour, the C5 epimer from Example 1, step D (167 mg, 0.305 mmol) was added in 0.5 mL THF via syringe and was followed by the addition of thiobenzoic acid (110 µL, 0.914 mmol) via syringe. This orange solution was stirred for 22 hours at room temperature. After removal of solvents in vacuo, the residue was purified by flash chromatography (0 to 10% ethyl acetate/hexanes gradient) to provide the title compound as a light yellow oil (104 mg, 50% yield). MS (ES+) [M+NH$_4$]$^+$=566.

B. Preparation of (2S,3R,4R,5S,6R)-2-(4-chloro-3-(4-ethoxybenzyl)phenyl)-6-methoxytetrahydro-2H-thiopyran-3,4,5-triol. Sodium methoxide (0.3 mL of a 4.3M solution in methanol) was added to a solution of the compound from Step A (104 mg, 0.152 mmol) in 6 mL methanol. After 30 minutes, the reaction was diluted with 20 mL ethyl acetate and washed with water and brine (20 mL each). The organic layer was dried with magnesium sulfate, filtered and solvents removed in vacuo. The residue was purified quickly by flash chromatography (5% ethyl acetate/hexanes) and the product was carried on directly to prevent disulfide formation.

One drop of acetyl chloride was added to 1 mL of methanol and stirred for 15 minutes at room temperature. This acidic solution was added to the free thiol from above and heated for 42 hours at 80° C. The reaction was cooled to room temperature and the solvent was removed in vacuo. The crude residue was purified by prep HPLC (30×250 mm C18 column, 5-75% acetonitrile:water (10 mM ammonium acetate), 15 minutes, 45 mL/min) to afford the title compound (alpha anomer, t=13.82 minutes, 8.7 mg, 13% yield for 2 steps).

$^1$H NMR (400 MHz, acetone-d$_6$) δ ppm 7.33 (m, 2H), 7.25 (dd, J=2.27, 8.34 Hz, 1H), 7.13 (d, J=8.59 Hz, 2H), 6.82 (d, J=8.59 Hz, 2H), 4.48 (d, J=3.03 Hz, 1H), 4.02 (s, 2H), 3.99 (q, J=7.07 Hz, 2H), 3.91 (d, J=10.36 Hz, 1H), 3.80-3.85 (m, 2H), 3.68 (dd, J=8.37, 9.35 Hz, 1H), 3.42 (s, 3H), 1.33 (t, J=7.07 Hz, 3H). MS (ES+) [M+NH$_4$]$^+$=424.

6.22. Example 22

Synthesis of (2S,3S,4R,5R,6R)-2-[4-Chloro-3-(4-ethoxy-benzyl)-phenyl]-6-hydroxymethyl-piperidine-3,4,5-triol

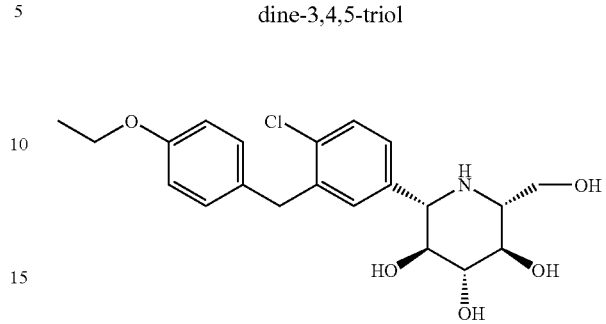

A. Preparation of (2R,3R,4S,5R,6S)-3,4,5-tris-allyloxy-2-allyloxymethyl-6-methoxy-tetrahydro-pyran. To a solution of α-D-methylglucoside (3 g, 15.45 mmol) in DMF (50 ml) was added NaH (60% dispersion in mineral oil, 3.34 g, 0.14 mol). During this addition, a thick suspension forms and an additional amount of DMF (15 ml) was added to get back into solution. After stirring at room temperature for 30 minutes, the mixture was cooled to 0° C. and allyl bromide (17 g, 0.14 mol, 12 ml) was added slowly. The mixture was then allowed to warm to room temperature and stirred for 18 hours. MeOH was carefully added to the light brown mixture to quench excess NaH and then the mixture was concentrated. The residue was diluted with CH$_2$Cl$_2$ and washed with H$_2$O, dried (MgSO$_4$) and concentrated to afford a yellow oil. Purification by silica gel chromatography (20% EtOAc/hexanes) afforded (2R,3R,4S,5R,6S)-3,4,5-tris-allyloxy-2-allyloxymethyl-6-methoxy-tetrahydro-pyran (4.06 g, 11.47 mmol, 74%) as a colorless oil. TLC: R$_f$=0.20, 20% EtOAc/hexanes.

B. Preparation of (3R,4S,5R,6R)-3,4,5-tris-allyloxy-6-allyloxymethyl-tetrahydro-pyran-2-ol. A solution of compound from Step A (10 g, 0.028 mol) in AcOH (400 ml) was warmed to 90° C. TfOH (2 N solution in H$_2$O, 16.69 g, 0.112 mol, 56 ml) was added and the mixture stirred at 90° C. for 75 minutes. The solution was cooled and diluted with CH$_2$Cl$_2$, washed with H$_2$O (x3), NaHCO$_3$ sat., dried (MgSO$_4$) and concentrated to give a yellow solid. Purification by silica gel chromatography (20%-40% EtOAc/hexanes) afforded (3R, 4S,5R,6R)-3,4,5-tris-allyloxy-6-allyloxymethyl-tetrahydro-pyran-2-ol as a mixture of anomers (5.85 g, 17.2 mmol, 61%) as a white solid. TLC: R$_f$=0.40, 40% EtOAc/hexanes.

C. Preparation of (3R,4S,5R,6R)-3,4,5-tris-allyloxy-6-allyloxymethyl-tetrahydro-pyran-2-one. Oxalyl chloride (2.75 g, 21.7 mmol, 1.89 ml) was dissolved in CH$_2$Cl$_2$ (90 ml) and the mixture cooled to −78° C. DMSO (3.39 g, 43.4 mmol, 3.08 ml) was added as a solution in CH$_2$Cl$_2$ (60 ml). The mixture was stirred at −78° C. for 15 minutes and then compound from Step B (6.70 g, 19.7 mmol) was added as a solution in CH$_2$Cl$_2$ (150 ml). The reaction mixture was stirred for a further 15 minutes at −78° C. and Et$_3$N (9.97 g, 98.5 mmol, 13.7 ml) added. The mixture was stirred at −78° C. for a further 5 minutes and then allowed to warm to room temperature over 30 minutes. The reaction was quenched with H$_2$O and the organic layer separated, washed twice with H$_2$O, dried and concentrated to give a pale yellow oil. Purification by silica gel chromatography (15% EtOAc/hexanes) afforded (3R,4S,5R,6R)-3,4,5-tris-allyloxy-6-allyloxymethyl-tetrahydro-pyran-2-one (2.49 g, 7.37 mmol, 37%) as a colorless oil. TLC: R$_f$=0.40, 20% EtOAc/hexanes.

D. Preparation of (3R,4S,5R,6R)-3,4,5-tris-allyloxy-6-allyloxymethyl-2-[4-chloro-3-(4-ethoxy-benzyl)-phenyl]-tetrahydro-pyran-2-ol. Compound from Example 1, Step C (2.37 g, 7.31 mmol) was dissolved in THF (25 ml) and cooled to −78° C. n-BuLi (2.5 N solution in hexanes, 0.47 g, 7.31 mmol, 2.92 ml) was added dropwise and the solution stirred for 15 minutes. Compound from Step C (2.47 g, 7.31 mmol) was added as a solution in THF (25 ml) and the reaction mixture stirred at −78° C. for a further 15 minutes before being allowed to warm to room temperature over 30 minutes. The reaction was quenched with NH$_4$Cl sat. and the organic layer separated. The aqueous layer was back extracted with Et$_2$O and the combined organics dried and concentrated to give a yellow oil. Purification by silica gel chromatography (10%-20% EtOAc/hexanes) afforded (3R,4S,5R,6R)-3,4,5-tris-allyloxy-6-allyloxymethyl-2-[4-chloro-3-(4-ethoxy-benzyl)-phenyl]-tetrahydro-pyran-2-ol (0.95 g, 1.63 mmol, 22%) as a colorless oil. MS (ES+) [M+NH$_4$]$^+$=602.

E. Preparation of (2R,3R,4S)-2,3,4,6-tetrakis-allyloxy-1-[4-chloro-3-(4-ethoxy-benzyl)-phenyl]-hexane-1,5-dione. To a solution of compound from Step D (0.93 g, 1.59 mmol) in CH$_2$Cl$_2$ (25 ml) was added Dess-Martin periodinane (0.68 g, 1.59 mmol). The mixture was stirred at room temperature for 1 hour and then a second portion of Dess-Martin periodinane (1 eqiv.) was added. Stirring was continued for another hour and then the reaction was quenched with 1N NaOH (~4 ml). H$_2$O was added and the organic layer separated. The aqueous layer was back extracted with CH$_2$Cl$_2$, dried and concentrated to give a yellow waxy solid. Purification by silica gel chromatography (15%-20% EtOAc/hexanes) afforded (2R,3R,4S)-2,3,4,6-tetrakis-allyloxy-1-[4-chloro-3-(4-ethoxy-benzyl)-phenyl]-hexane-1,5-dione (0.60 g, 1.03 mmol, 65%) as a white solid. MS (ES+) [M+NH$_4$]$^+$=600.

F. Preparation of (2R,3R,4R,5S,6S)-3,4,5-tris-allyloxy-2-allyloxymethyl-6-[4-chloro-3-(4-ethoxy-benzyl)-phenyl]-piperidine. To a solution of compound from Step E (0.60 g, 1.03 mmol) in MeOH (12 ml) was added 4 Å MS followed by ammonium formate (0.13 g, 2.06 mmol). NaBH$_3$CN (0.14 g, 2.3 mmol) was then added in one portion and the mixture stirred at room temperature for 1 hour 30 minutes. The reaction mixture was then filtered and concentrated. Purification by silica gel chromatography (10%-20% EtOAc/hexanes) afforded (2R,3R,4R,5S,6S)-3,4,5-tris-allyloxy-2-allyloxymethyl-6-[4-chloro-3-(4-ethoxy-benzyl)-phenyl]-piperidine (155 mg, 0.27 mmol, 27%). MS (ES+) [M+H]$^+$=568.

G. Preparation of (2S,3S,4R,5R,6R)-2-[4-chloro-3-(4-ethoxy-benzyl)-phenyl]-3,4,5-tris-[((E)-prop enyl)oxy]-6-[((E)-prop enyl)oxymethyl]-piperidine. Ir(COD)[PCH$_3$Ph$_2$]PF$_6$ (8 mg, 30 mol %) in THF (0.3 ml) was stirred under an atmosphere of H$_2$ until the color changed from red to pale yellow (~5 minutes). Compound from Step F (19 mg, 0.033 mol) in THF (0.5 ml) was then added and the mixture stirred at room temperature for 45 minutes and then concentrated. Purification by silica gel chromatography (20% EtOAc/hexanes) afforded (2S,3S,4R,5R,6R)-2-[4-chloro-3-(4-ethoxy-benzyl)-phenyl]-3,4,5-tris-[((E)-propenyl)oxy]-6-[((E)-propenyl)oxymethyl]-piperidine (15 mg, 0.026 mmol, 80%) as a colorless oil. MS (ES+) [M+H]$^+$=568.

H. Preparation of (2S,3S 4R,5R,6R)-2-[4-chloro-3-(4-ethoxy-benzyl)-phenyl]-6-hydroxymethyl-piperidine-3,4,5-triol. Compound from Step G (15 mg, 0.026 mmol) was dissolved in a solution of THF/AcOH/1NHCl (0.2 ml:0.3 ml:0.15 ml) and heated to 70° C. for 30 minutes. The mixture was concentrated to give a pale yellow oil. Purification by preparative HPLC (sunfire C18, 30×100 mm, 5 μm, 10%-100% B over 15 minutes) afforded (2S,3S,4R,5R,6R)-2-[4-chloro-3-(4-ethoxy-benzyl)-phenyl]-6-hydroxymethyl-piperidine-3,4,5-triol (5 mg, 0.012 mmol, 46%) as a white solid. MS (ES+) [M+H]$^+$=408.

$^1$H NMR (400 MHz, MeOD) δ ppm 7.36 (m, 2H), 7.28 (m, 1H), 7.12 (d, J=8.6 Hz, 2H), 6.81 (d, J=8.6 Hz, 2H), 4.05 (m, 2H), 4.00 (q, J=6.8 Hz, 2H), 3.92 (dd, J=3.0 Hz and 10.8 Hz, 1H), 3.58 (dd, J=7.6 Hz and 11.1 Hz, 1H), 3.47 (m, 1H), 3.26-3.36 (m, 3H), 2.70 (m, 1H), 1.37 (t, J=7.1 Hz, 3H).

6.23. Example 23

Synthesis of (2S,3S,4R,5R,6R)-2-[4-Chloro-3-(4-ethoxy-benzyl)-phenyl]-6-hydroxymethyl-1-methyl-piperidine-3,4,5-triol

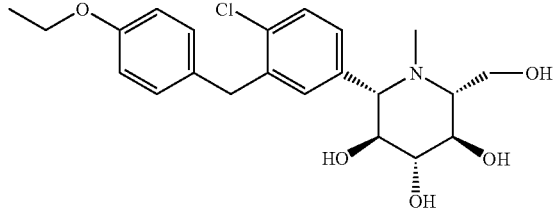

A. Preparation of (2R,3R,4R,5S,6S)-3,4,5-tris-allyloxy-2-allyloxymethyl-6-[4-chloro-3-(4-ethoxy-benzyl)-phenyl]-1-methyl-piperidine. To a solution of compound from Example 22, Step F (135 mg, 0.24 mmol) in MeCN was added K$_2$CO$_3$ (164 mg, 1.19 mmol). The mixture was stirred for 30 minutes and then MeI (676 mg, 4.76 mmol) was added. Stirring was continued at room temperature for 8 hours, then the mixture was filtered and concentrated. Purification by silica gel chromatography (10% EtOAc/hexanes) afforded (2R,3R,4R,5S, 6S)-3,4,5-tris-allyloxy-2-allyloxymethyl-6-[4-chloro-3-(4-ethoxy-benzyl)-phenyl]-1-methyl-piperidine (90 mg, 0.15 mmol, 65%) as a colorless oil. MS (ES+) [M+H]$^+$=582.

B. Preparation of (2S,3S,4R,5R,6R)-2-[4-chloro-3-(4-ethoxy-benzyl)-phenyl]-1-methyl-3,4,5-tris-[((E)-propenyl)oxy]-6-[((E)-propenyl)oxymethyl]-piperidine. Ir(COD)[PCH$_3$Ph$_2$]PF$_6$ (27 mg, 30 mol %) in THF (1 ml) was stirred under an atmosphere of H$_2$ until the color changed from red to pale yellow (~5 minutes). Compound from Step A (62 mg, 0.11 mol) in THF (1.5 ml) was then added and the mixture stirred at room temperature for 45 minutes and then concentrated. Purification by silica gel chromatography (20% EtOAc/hexanes) afforded (2S,3S,4R,5R,6R)-2-[4-chloro-3-(4-ethoxy-benzyl)-phenyl]-1-methyl-3,4,5-tris-[((E)-propenyl)oxy]-6-[((E)-propenyl)oxymethyl]-piperidine (62 mg, 0.11 mmol, 100%) as a colorless oil. MS (ES+) [M+H]$^+$=582.

C. Preparation of (2S,3S,4R,5R,6R)-2-[4-chloro-3-(4-ethoxy-benzyl)-phenyl]-6-hydroxymethyl-1-methyl-piperidine-3,4,5-triol. Compound from Step B (54 mg, 0.093 mmol) was dissolved in a solution of THF/AcOH/1NHCl (0.5 ml:0.6 ml:0.30 ml) and heated to 70° C. for 30 minutes. The mixture was concentrated to give a pale yellow oil. Purification by preparative HPLC (sunfire C18, 30×100 mm, 5 μm, 10%-100% B over 15 minutes) afforded (2S,3S,4R,5R,6R)-2-[4-chloro-3-(4-ethoxy-benzyl)-phenyl]-6-hydroxymethyl-1-methyl-piperidine-3,4,5-triol (22 mg, 0.052 mmol, 56%) as a white solid. MS (ES+) [M+H]$^+$=422.

$^1$H NMR (400 MHz, MeOD) δ ppm 7.31 (m, 2H), 7.22 (m, 1H), 7.07 (d, J=8.8 Hz, 2H), 6.77 (d, J=8.8 Hz, 2H), 4.00 (m, 2H), 3.96 (q, J=7.1 Hz, 2H), 3.90 (m, 2H), 3.52 (dd, J=9.4 Hz and 9.4 Hz, 1H), 3.23-3.32 (m, 3H), 2.88 (d, J=8.8 Hz, 1H), 2.00 (s, 3H), 1.34 (t, J=7.1 Hz, 3H).

6.24. Additional Compounds

Using the procedures described herein and methods known in the art, the additional compounds listed below in Table 1 were prepared. Potent SGLT2 inhibitors are marked with an asterisk.

TABLE 1

| Compound | Molecular Formula | MS (M + H)+ |
|---|---|---|
| (2S,3R,4R,5S)-2-[3-(4-Ethoxy-benzyl)-phenyl]-6-methoxy-tetrahydro-pyran-3,4,5-triol* | $C_{21}H_{26}O_6$ | 374 |
| (2S,3R,4R,5S,6S)-2-[4-Chloro-3-(4-ethoxy-benzyl)-phenyl]-6-(2-hydroxy-ethoxy)-tetrahydro-pyran-3,4,5-triol* | $C_{22}H_{27}ClO_7$ | 438.1 |
| (3S,4R,5R,6S)-2-Benzyloxy-6-[4-chloro-3-(4-ethoxy-benzyl)-phenyl]-tetrahydro-pyran-3,4,5-triol* | $C_{27}H_{29}ClO_6$ | 484.1 |
| (2S,3R,4R,5S)-2-(4'-Ethoxy-biphenyl-3-yl)-6-methoxy-tetrahydro-pyran-3,4,5-triol* | $C_{20}H_{24}O_6$ | 378 (M + NH$_3$)+ |
| (2S,3R,4R,5S)-2-[4-Chloro-3-(4-ethoxy-benzyl)-phenyl]-6-(2,2,2-trifluoro-ethoxy)-tetrahydro-pyran-3,4,5-triol* | $C_{22}H_{24}ClF_3O_6$ | 476.1 |
| (2S,3R,4R,5S)-2-[4-Chloro-3-(4-ethoxy-benzyl)-phenyl]-6-(2-methoxy-ethoxy)-tetrahydro-pyran-3,4,5-triol* | $C_{23}H_{29}ClO_7$ | 452.1 |
| (2S,3R,4R,5S)-2-[4-Chloro-3-(4-ethoxy-benzyl)-phenyl]-6-(2-dimethylamino-ethoxy)-tetrahydro-pyran-3,4,5-triol* | $C_{24}H_{32}ClNO_6$ | 466.1 |
| (2S,3R,4R,5S)-2-[4-Chloro-3-(4-ethoxy-benzyl)-phenyl]-6-propylsulfanyl-tetrahydro-pyran-3,4,5-triol* | $C_{23}H_{29}ClO_5S$ | 452 |
| (2S,3R,4R,5S)-2-[4-Chloro-3-(4-ethoxy-benzyl)-phenyl]-6-imidazol-1-yl-tetrahydro-pyran-3,4,5-triol* | $C_{23}H_{25}ClN_2O_5$ | 445.1 |
| {(3S,4R,5R,6S)-6-[4-Chloro-3-(4-ethoxy-benzyl)-phenyl]-3,4,5-trihydroxy-tetrahydro-pyran-2-yloxy}-acetic acid methyl ester* | $C_{23}H_{27}ClO_8$ | 466.1 |
| (2S,3R,4R,5S)-2-[4-Chloro-3-(4-ethoxy-benzyl)-phenyl]-6-(4-methyl-piperidin-1-yl)-tetrahydro-pyran-3,4,5-triol | $C_{26}H_{34}ClNO_5$ | 475.1 |
| (2S,3R,4R,5S)-2-[4-Chloro-3-(4-ethoxy-benzyl)-phenyl]-6-(5-methyl-thiazol-2-ylamino)-tetrahydro-pyran-3,4,5-triol | $C_{24}H_{27}ClN_2O_5S$ | 491 |
| (2S,3R,4R,5S,6R)-2-[4-Chloro-3-(4-ethoxy-benzyl)-phenyl]-6-phenoxy-tetrahydro-pyran-3,4,5-triol* | $C_{26}H_{27}ClO_6$ | 470.1 |
| N-{(2S,3S,4R,5R,6S)-6-[4-Chloro-3-(4-ethoxy-benzyl)-phenyl]-3,4,5-trihydroxy-tetrahydro-pyran-2-yl}-N-methyl-acetamide | $C_{23}H_{28}ClNO_6$ | 450 |
| Acetic acid (2S,3S,4R,5S,6S)-4,5-diacetoxy-6-[4-chloro-3-(4-ethoxy-benzyl)-phenyl]-2-methoxy-tetrahydro-pyran-3-yl ester | $C_{27}H_{31}ClO_9$ | 552 (M + NH$_3$)+ |
| (2S,3R,4R,5S)-2-[4-Chloro-3-(4-ethoxy-phenoxy)-phenyl]-6-methoxy-tetrahydro-pyran-3,4,5-triol | $C_{20}H_{23}ClO_7$ | 428 (M + NH$_3$)+ |
| (2S,3R,4R,5S)-2-[4-Chloro-3-(4-methoxy-phenylsulfanyl)-phenyl]-6-methoxy-tetrahydro-pyran-3,4,5-triol* | $C_{19}H_{21}ClO_6S$ | 430 (M + NH$_3$)+ |
| (2S,3R,4R,5S)-2-[4-Chloro-3-(4-methoxy-benzenesulfinyl)-phenyl]-6-methoxy-tetrahydro-pyran-3,4,5-triol | $C_{19}H_{21}ClO_7S$ | 429 |
| (2S,3R,4R,5S)-2-[4-Chloro-3-(4-ethoxy-benzyl)-phenyl]-6-(3-hydroxy-propoxy)-tetrahydro-pyran-3,4,5-triol* | $C_{23}H_{29}ClO_7$ | 452.2 |
| (2S,3R,4R,5S,6R)-2-[4-Chloro-3-(4-ethoxy-benzyl)-phenyl]-6-(2-hydroxy-ethylsulfanyl)-tetrahydro-pyran-3,4,5-triol* | $C_{22}H_{27}ClO_6S$ | 472 (M + NH$_3$)+ |
| (2S,3R,4R,5S)-2-[4-Chloro-3-(4-ethoxy-benzyl)-phenyl]-6-(2-mercapto-ethoxy)-tetrahydro-pyran-3,4,5-triol* | $C_{22}H_{27}ClO_6S$ | 456.3 |
| (2S,3R,4R,5S)-2-[4-Chloro-3-(4-ethoxy-benzyl)-phenyl]-6-(2,3-dihydroxy-propoxy)-tetrahydro-pyran-3,4,5-triol* | $C_{23}H_{29}ClO_8$ | 468.2 |
| (2S,3R,4R,5S)-2-{4-Chloro-3-[4-(2-methoxy-ethoxy)-benzyl]-phenyl}-6-methoxy-tetrahydro-pyran-3,4,5-triol* | $C_{22}H_{27}ClO_7$ | 456 (M + NH$_3$)+ |
| (2S,3R,4R,5S,6R)-2-[4-Chloro-3-(4-ethoxy-benzyl)-phenyl]-6-ethylsulfanyl-tetrahydro-pyran-3,4,5-triol* | $C_{22}H_{27}ClO_5S$ | 456 (M + NH$_3$)+ |
| (2S,3R,4R,5S,6R)-2-[4-Chloro-3-(4-ethoxy-benzyl)-phenyl]-6-methylsulfanyl-tetrahydro-pyran-3,4,5-triol* | $C_{21}H_{25}ClO_5S$ | 442 (M + NH$_3$)+ |
| [2-Chloro-5-((2S,3R,4R,5S,6S)-3,4,5-trihydroxy-6-methoxy-tetrahydro-pyran-2-yl)-phenyl]-(4-ethoxy-phenyl)-methanone* | $C_{21}H_{23}ClO_7$ | 423 |
| (2S,3R,4R,5S,6S)-2-{4-Chloro-3-[(4-ethoxy-phenyl)-hydroxy-methyl]-phenyl}-6-methoxy-tetrahydro-pyran-3,4,5-triol* | $C_{21}H_{25}ClO_7$ | 407 |
| (2S,3R,4R,5S)-2-[3-(4-Ethoxy-benzyl)-4-methyl-phenyl]-6-methoxy-tetrahydro-pyran-3,4,5-triol* | $C_{22}H_{28}O_6$ | 406 (M + NH$_3$)+ |
| (2S,3R,4R,5S)-2-{4-Chloro-3-[4-(2-methylsulfanyl-ethoxy)-benzyl]-phenyl}-6-methoxy-tetrahydro-pyran-3,4,5-triol* | $C_{22}H_{27}ClO_6S$ | 472 (M + NH$_3$)+ |
| (2S,3R,4R,5S)-2-{4-Chloro-3-[4-(pyridin-4-yloxy)-benzyl]-phenyl}-6-methoxy-tetrahydro-pyran-3,4,5-triol* | $C_{24}H_{24}ClNO_6$ | 458 |
| (2S,3R,4R,5S,6S)-2-(4-Chloro-3-{(4-ethoxy-phenyl)-[(Z)-propylimino]-methyl}-phenyl)-6-methoxy-tetrahydro-pyran-3,4,5-triol | $C_{24}H_{30}ClNO_6$ | 464 |
| (2S,3R,4R,5S)-2-{4-Chloro-3-[4-(thiazol-2-yloxy)-benzyl]-phenyl}-6-methoxy-tetrahydro-pyran-3,4,5-triol* | $C_{22}H_{22}ClNO_6S$ | 464 |

TABLE 1-continued

| Compound | Molecular Formula | MS (M + H)+ |
|---|---|---|
| (2S,3R,4R,5S)-2-{4-Chloro-3-[4-(pyrimidin-5-yloxy)-benzyl]-phenyl}-6-methoxy-tetrahydro-pyran-3,4,5-triol* | $C_{23}H_{23}ClN_2O_6$ | 459 |
| (2S,3R,4R,5S)-2-{4-Chloro-3-[4-(2,6-dimethoxy-pyrimidin-4-yloxy)-benzyl]-phenyl}-6-methoxy-tetrahydro-pyran-3,4,5-triol* | $C_{25}H_{27}ClN_2O_8$ | 519 |
| 2-{(2R,3S,4R,5R,6S)-6-[4-Chloro-3-(4-ethoxy-benzyl)-phenyl]-3,4,5-trihydroxy-tetrahydro-pyran-2-ylsulfanyl}-acetamide* | $C_{22}H_{26}ClNO_6S$ | 468.1 |
| (2S,3R,4R,5S,6R)-2-[4-Chloro-3-(4-ethoxy-benzyl)-phenyl]-6-(furan-2-ylmethylsulfanyl)-tetrahydro-pyran-3,4,5-triol* | $C_{25}H_{27}ClO_6S$ | 490.1 |
| (2S,3R,4R,5S,6S)-2-{4-Chloro-3-[(4-ethoxy-phenyl)-imino-methyl]-phenyl}-6-methoxy-tetrahydro-pyran-3,4,5-triol | $C_{21}H_{24}ClNO_6$ | 422 |
| (2S,3R,4R,5S,6S)-2-{3-[(4-Ethoxy-phenyl)-hydroxy-methyl]-phenyl}-6-methoxy-tetrahydro-pyran-3,4,5-triol | $C_{21}H_{26}O_7$ | 390 |
| (2S,3S,4S,5R)-2-[4-Chloro-3-(4-ethoxy-benzyl)-phenyl]-3,4,5-trihydroxy-piperidine-1-carboxylic acid benzyl ester | $C_{28}H_{30}ClNO_6$ | 511 |
| (2S,3S,4S,5R)-2-[4-Chloro-3-(4-ethoxy-benzyl)-phenyl]-3,4,5-trihydroxy-piperidine-1-carboxylic acid allylamide* | $C_{24}H_{29}ClN_2O_5$ | 461 |
| N-(2-{(2R,3S,4R,5R,6S)-6-[4-Chloro-3-(4-ethoxy-benzyl)-phenyl]-3,4,5-trihydroxy-tetrahydro-pyran-2-ylsulfanyl}-ethyl)-acetamide* | $C_{24}H_{30}ClNO_6S$ | 496.1 |
| (2S,3R,4R,5S,6R)-2-[4-Chloro-3-(4-ethoxy-benzyl)-phenyl]-6-(2,2,2-trifluoro-ethylsulfanyl)-tetrahydro-pyran-3,4,5-triol* | $C_{22}H_{24}ClF_3O_5S$ | 492.1 |
| (2S,3R,4R,5S,6S)-2-{4-Chloro-3-[1-(4-ethoxy-phenyl)-1-hydroxy-ethyl]-phenyl}-6-methoxy-tetrahydro-pyran-3,4,5-triol | $C_{22}H_{27}ClO_7$ | 438 |
| Dimethyl-thiocarbamic acid O-{4-[2-chloro-5-((2S,3R,4R,5S)-3,4,5-trihydroxy-6-methoxy-tetrahydro-pyran-2-yl)-benzyl]-phenyl} ester* | $C_{22}H_{26}ClNO_6S$ | 468 |
| (2S,3R,4R,5S,6S)-2-{3-[1-(4-Ethoxy-phenyl)-ethyl]-phenyl}-6-methoxy-tetrahydro-pyran-3,4,5-triol | $C_{22}H_{28}O_6$ | 406 (M + NH$_3$)+ |
| Diethyl-dithiocarbamic acid (2R,3S,4R,5R,6S)-6-[4-chloro-3-(4-ethoxy-benzyl)-phenyl]-3,4,5-trihydroxy-tetrahydro-pyran-2-yl ester | $C_{25}H_{32}ClNO_5S_2$ | 526.2 |
| (2S,3R,4R,5S,6S)-2-(4-Chloro-3-{4-[(R)-(tetrahydro-furan-3-yl)oxy]-benzyl}-phenyl)-6-methoxy-tetrahydro-pyran-3,4,5-triol* | $C_{23}H_{27}ClO_7$ | 468 (M + NH$_3$)+ |
| (2S,3R,4R,5S,6R)-2-[4-Chloro-3-(4-ethoxy-benzyl)-phenyl]-6-ethanesulfinyl-tetrahydro-pyran-3,4,5-triol* | $C_{22}H_{27}ClO_6S$ | 455 |
| (2S,3R,4R,5S)-2-{4-Chloro-3-[4-((S)-1-methyl-pyrrolidin-3-yloxy)-benzyl]-phenyl}-6-methoxy-tetrahydro-pyran-3,4,5-triol* | $C_{24}H_{30}ClNO_6$ | 522 (M − H + Ac) |
| (2S,3R,4R,5S)-2-{4-Chloro-3-[4-(tetrahydro-pyran-4-yloxy)-benzyl]-phenyl}-6-methoxy-tetrahydro-pyran-3,4,5-triol* | $C_{24}H_{29}ClO_7$ | 523 (M − H + Ac) |
| (2S,3R,4R,5S)-2-(4-Chloro-{4-hydroxy-3-[1-(2-methylamino-ethyl)-allyl]-benzyl}-phenyl)-6-methoxy-tetrahydro-pyran-3,4,5-triol | $C_{25}H_{32}ClNO_6$ | 478 |
| (2S,3R,4R,5S)-2-{4-Chloro-3-[4-(1-methyl-piperidin-4-yloxy)-benzyl]-phenyl}-6-methoxy-tetrahydro-pyran-3,4,5-triol* | $C_{25}H_{32}ClNO_6$ | 478 |
| (2S,3R,4R,5S,6R)-2-[4-Chloro-3-(4-ethoxy-benzyl)-phenyl]-6-methanesulfinyl-tetrahydro-pyran-3,4,5-triol* | $C_{21}H_{25}ClO_6S$ | 441 |
| (2S,3S,4S,5R)-1-Benzyl-2-[4-chloro-3-(4-ethoxy-benzyl)-phenyl]-piperidine-3,4,5-triol* | $C_{27}H_{30}ClNO_4$ | 468 |
| (2S,3R,4R,5S)-2-{3-[4-(2-Benzyloxy-ethoxy)-benzyl]-4-chloro-phenyl}-6-methoxy-tetrahydro-pyran-3,4,5-triol* | $C_{28}H_{31}ClO_7$ | 532 (M + NH$_3$)+ |
| (2S,3R,4R,5S)-2-{3-[4-(2-Hydroxy-ethoxy)-benzyl]-phenyl}-6-methoxy-tetrahydro-pyran-3,4,5-triol* | $C_{21}H_{26}O_7$ | 408 (M + NH$_3$)+ |
| (2S,3R,4R,5S)-2-{4-Chloro-3-[4-(2-hydroxy-ethoxy)-benzyl]-phenyl}-6-methoxy-tetrahydro-pyran-3,4,5-triol* | $C_{21}H_{25}ClO_7$ | 442 (M + NH$_3$)+ |
| 2-{(2S,3S,4S,5R)-2-[4-Chloro-3-(4-ethoxy-benzyl)-phenyl]-3,4,5-trihydroxy-piperidin-1-yl}-acetamide* | $C_{22}H_{27}ClN_2O_5$ | 435 |
| (2S,3S,4S,5R)-2-[4-Chloro-3-(4-ethoxy-benzyl)-phenyl]-1-isobutyl-piperidine-3,4,5-triol* | $C_{24}H_{32}ClNO_4$ | 492 (M − H + Ac) |
| (2S,3R,4R,5S,6R)-2-[4-Chloro-3-(4-ethoxy-benzyl)-phenyl]-6-(2-methyl-tetrahydro-furan-3-ylsulfanyl)-tetrahydro-pyran-3,4,5-triol* | $C_{25}H_{31}ClO_6S$ | 512 (M + NH$_3$)+ |
| (R)-2-Amino-3-{(2R,3S,4R,5R,6S)-6-[4-chloro-3-(4-ethoxy-benzyl)-phenyl]-3,4,5-trihydroxy-tetrahydro-pyran-2-ylsulfanyl}-propionic acid* | $C_{23}H_{28}ClNO_7S$ | 498 |

TABLE 1-continued

| Compound | Molecular Formula | MS (M + H)+ |
|---|---|---|
| (2S,3R,4R,5S,6R)-2-[4-Chloro-3-(4-ethoxy-benzyl)-phenyl]-6-cyclopentylsulfanyl-tetrahydro-pyran-3,4,5-triol* | $C_{25}H_{31}ClO_5S$ | 496 (M + NH$_3$)+ |
| (2S,3R,4R,5S,6R)-2-[4-Chloro-3-(4-ethoxy-benzyl)-phenyl]-6-cyclohexylsulfanyl-tetrahydro-pyran-3,4,5-triol | $C_{26}H_{33}ClO_5S$ | 510 (M + NH$_3$)+ |
| (2S,3R,4R,5S,6R)-2-[4-Chloro-3-(4-ethoxy-benzyl)-phenyl]-6-(3-methyl-butylsulfanyl)-tetrahydro-pyran-3,4,5-triol* | $C_{25}H_{33}ClO_5S$ | 498 (M + NH$_3$)+ |
| (2S,3R,4R,5S)-2-[3-(4-Ethoxy-benzyl)-phenyl]-6-methoxy-tetrahydro-pyran-3,4,5-triol* | $C_{27}H_{31}ClO_9$ | 552 (M + NH$_3$)+ |
| 1-{(2S,3S,4S,5R)-2-[4-Chloro-3-(4-ethoxy-benzyl)-phenyl]-3,4,5-trihydroxy-piperidin-1-yl}-ethanone* | $C_{22}H_{26}ClNO_5$ | 420 |
| (2S,3S,4S,5R)-2-[4-Chloro-3-(4-ethoxy-benzyl)-phenyl]-3,4,5-trihydroxy-piperidine-1-carboxylic acid benzyl ester | $C_{28}H_{30}ClNO_6$ | 529 [M + NH$_4$]+ |
| (2S,3S,4S,5R)-1-Benzyl-2-[4-chloro-3-(4-ethoxy-benzyl)-phenyl]-piperidine-3,4,5-triol* | $C_{27}H_{30}ClNO_4$ | 468 |
| 2-{(2S,3S,4S,5R)-2-[4-Chloro-3-(4-ethoxy-benzyl)-phenyl]-3,4,5-trihydroxy-piperidin-1-yl}-acetamide* | $C_{22}H_{27}ClN_2O_5$ | 435 |
| (2S,3S,4S,5R)-2-[4-Chloro-3-(4-ethoxy-benzyl)-phenyl]-1-isobutyl-piperidine-3,4,5-triol* | $C_{24}H_{32}ClNO_4$ | 492 [M + Ac]− |
| (3S,4R,5R)-2-[4-Chloro-3-(4-ethoxy-benzyl)-phenyl]-6-hydroxymethyl-piperidine-3,4,5-triol* | $C_{21}H_{26}ClNO_5$ | 408 |

6.25. In Vitro Human SGLT2 Inhibition Assay

Human sodium/glucose co-transporter type 2 (SGLT2; accession number P31639; GI:400337) was cloned into pIRESpuro2 vector for mammalian expression (construct: HA-SGLT2-pIRESpuro2).

HEK293 cells were transfected with the human HA-SGLT2-pIRESpuro2 vector and the bulk stable cell line was selected in presence of 0.5 µg/ml of puromycin. Human HA-SGLT2 cells were maintained in DMEM media containing 10% FBS, 1% GPS and 0.5 µg/ml of puromycin.

The HEK293 cells expressing the human HA-SGLT2 were seeded in 384 well plates (30,000 cells/well) in DMEM media containing 10% FBS, 1% GPS and 0.5 µg/ml of puromycin, then incubated overnight at 37 C., 5% $CO_2$. Cells were then washed with uptake buffer (140 mM NaCl, 2 mM KCl, 1 mM $CaCl_2$, 1 mM $MgCl_2$, 10 mM HEPES, 5 mM Tris, 1 mg/ml bovine serum albumin (BSA), pH 7.3). Twenty microliters of uptake buffer with or without testing compounds were added to the cells. Then, 20 microliters of uptake buffer containing $^{14}$C-AMG (100 nCi) were added to the cells. The cell plates were incubated at 37° C., 5% $CO_2$ for 1-2 hours. After washing the cells with uptake buffer, scintillation fluid was added (40 microliters/well) and $^{14}$C-AMG uptake was measured by counting radioactivity using a scintillation coulter (Top-Coulter NXT; Packard Instruments).

6.26. In Vitro Human SGLT1 Inhibition Assay

Human sodium/glucose co-transporter type 1 (SGLT1; accession number NP_000334; GI: 4507031) was cloned into pIRESpuro2 vector for mammalian expression (construct: HA-SGLT1-pIRESpuro2).

HEK293 cells were transfected with the human HA-SGLT1-pIRESpuro2 vector and the bulk stable cell line was selected in presence of 0.5 µg/ml of puromycin. Human HA-SGLT1 cells were maintained in DMEM media containing 10% FBS, 1% GPS and 0.5 µg/ml of puromycin.

The HEK293 cells expressing the human HA-SGLT1 were seeded in 384 well plates (30,000 cells/well) in DMEM media containing 10% FBS, 1% GPS and 0.5 µg/ml of puromycin, then incubated overnight at 37 C., 5% $CO_2$. Cells were then washed with uptake buffer (140 mM NaCl, 2 mM KCl, 1 mM $CaCl_2$, 1 mM $MgCl_2$, 10 mM HEPES, 5 mM Tris, 1 mg/ml bovine serum albumin (BSA), pH 7.3). Twenty microliters of uptake buffer with or without testing compounds were added to the cells. Then, 20 microliters of uptake buffer containing $^{14}$C-AMG (100 nCi) were also added to cells. The cell plates were incubated at 37° C., 5% $CO_2$ for 1-2 hours. After washing the cells with uptake buffer, scintillation fluid was added (40 microliters/well) and $^{14}$C-AMG uptake was measured by counting radioactivity using a scintillation coulter (Top-Coulter NXT; Packard Instruments).

6.27. Calculating $IC_{50}$ Values

The $IC_{50}$ of a compound with regard to a given target is determined by fitting the relevant data, using the Levenburg Marquardt algorithm, to the equation:

$$y=A+((B-A)/(1+((C/x)^D)))$$

wherein A is the minimum y value; B is the maximum y value; C is the $IC_{50}$; and D is the slope. The calculation of the $IC_{50}$ is performed using XLFit4 software (ID Business Solutions Inc., Bridgewater, N.J. 08807) for Microsoft Excel (the above equation is model 205 of that software).

6.28. In Vivo Effect of Compounds

The pharmacological effects of compounds of the invention was determined using six drug-treated and six vehicle-treated c57 albino male mice weaned on 45% high fat diet and individually-housed in a Nalgene metabolic cage. The mice were provided drinking water and high-fat diet paste (2 parts diet to 1 part water) ad libitum.

Compounds were delivered two ways. In the first, mice were gavaged with drug or vehicle on day 1 with 5 ml/kg dose volume. The entire urine volume was collected for the following 24 hours into the metabolic cage plastic urine collector. Measures of mouse body weight, water consumption, food consumption (accounting for evaporation of water in the paste), and urine volume were made daily. Urine was collected daily, centrifuged, and assessed for glucose concentration using a Cobas Autoanalyzer. The final result of milligrams of glucose excreted per day was calculated from total urine volume and urine glucose concentration.

In the second method, compounds were delivered in the diet. This was done by mixing the test compound in the high fat diet paste at the appropriate concentration, when taking into account baseline body weight and baseline food consumption. Paste containing the drug was again provided in excess each day. The amount of compound delivered per day was confirmed by calculating animal body weight and food consumption.

FIG. 1 shows the effect of four compounds of the invention (A, B, C and D), when orally dosed once at 30 mg/kg, on the amount of excreted glucose during the 24 hours following dosing. By comparison, control animals excreted about 1 mg glucose over the 24 hours.

All publications (e.g., patents and patent applications) cited above are incorporated herein by reference in their entireties.

What is claimed is:

1. A compound of the formula

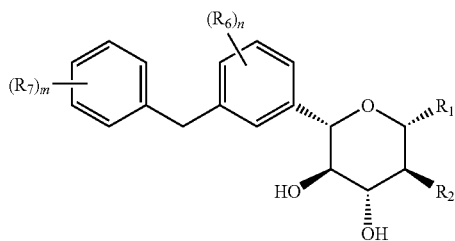

or a pharmaceutically acceptable salt thereof, wherein:
R1 is $N(R_{1A})_2$;
each $R_{1A}$ is independently hydrogen or optionally substituted alkyl, aryl or heterocycle;
$R_2$ is fluoro or $OR_{2A}$;
$R_{2A}$ is hydrogen, optionally substituted alkyl, C(O)alkyl, C(O)aryl, or aryl;
each $R_6$ is independently hydrogen, hydroxyl, halogen, amino, cyano, nitro, $C\equiv CR_{6A}$, $OR_{6A}$, $SR_{6A}$, $SOR_{6A}$, $SO_2R_{6A}$, $C(O)R_{6A}$, $CO_2R_{6A}$, $CO_2H$, $CON(R_{6A})(R_{6A})$, $CONH(R_{6A})$, $CONH_2$, $NHC(O)R_{6A}$, $NHSO_2R6_A$, or optionally substituted alkyl, aryl or heterocycle;
each $R_{6A}$ is independently optionally substituted alkyl, aryl or heterocycle;
each $R_7$ is independently hydrogen, hydroxyl, halogen, amino, cyano, nitro, $C\equiv CR_{7A}$, $OR_{7A}$, $SR_{7A}$, $SOR_{7A}$, $SO_2R_{7A}$, $C(O)R_{7A}$, $CO_2R_{7A}$, $CO_2H$, $CON(R_{7A})(R_{7A})$, $CONH(R_{7A})$, $CONH_2$, $NHC(O)R_{7A}$, $NHSO_2R_{7A}$, or optionally substituted alkyl, aryl or heterocycle;
each $R_{7A}$ is independently optionally substituted alkyl, aryl or heterocycle;
m is 1-3; and
n is 1-3.

2. The compound of claim 1, wherein at least one $R_{1A}$ is hydrogen.

3. The compound of claim 1, wherein at least one $R_{1A}$ is optionally substituted alkyl.

4. A compound of the formula:

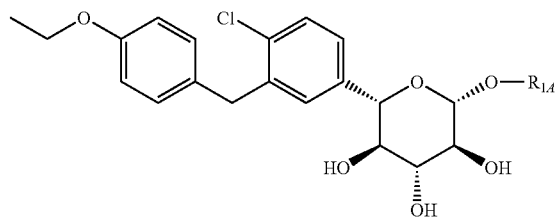

or a pharmaceutically acceptable salt thereof, wherein $R_{1A}$ is independently hydrogen or optionally substituted alkyl, aryl or heterocycle.

5. A compound of the formula:

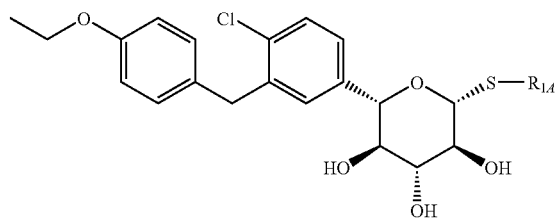

or a pharmaceutically acceptable salt thereof, wherein $R_{1A}$ is independently hydrogen or optionally substituted alkyl, aryl or heterocycle.

6. A compound of the formula:

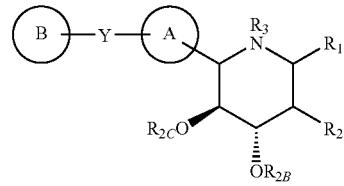

or a pharmaceutically acceptable salt thereof, wherein:
A is optionally substituted aryl, cycloalkyl, or heterocycle;
B is optionally substituted aryl, cycloalkyl, or heterocycle;
Y is O, S, SO, $SO_2$, $NR_4$, $(C(R_5)_2)_p$, $(C(R_5)_2)_q$—C(O)—$(C(R_5)_2)_q$, $(C(R_5)_2)_q$—C(O)O—$(C(R_5)_2)_q$, $(C(R_5)_2)_q$—OC(O)-(c(R_5)_2)q, $(C(R_5)_2)_q$—C(O)$NR_4$—$(C(R_5)_2)_q$, $(C(R_5)_2)_q$—$NR_4$C(O)—$(C(R_5)_2)_q$, or $(C(R_5)_2)_q$—$NR_4$C(O)$NR_4$—$(C(R_5)_2)_q$;
$R_1$ is $OR_{1A}$, $SR_{1A}$, $SOR_{1A}$, $SO_2R_{1A}$, or $R_{1A}$;
each $R_{1A}$ is independently hydrogen or optionally substituted alkyl, aryl or heterocycle;
$R_2$ is fluoro or $OR_{2A}$;
$R_3$ is hydrogen or optionally substituted alkyl, aryl or heterocycle, each of $R_{2A}$, $R_{2B}$, and $R_{2C}$ is independently hydrogen, optionally substituted alkyl, C(O)alkyl, C(O)aryl, or aryl;
each $R_4$ is independently hydrogen or optionally substituted alkyl;
each $R_5$ is independently hydrogen, hydroxyl, halogen, amino, cyano, $OR_{5A}$, $SR_{5A}$, or optionally substituted alkyl,
each $R_{5A}$ is independently optionally substituted alkyl;
p is 0-3;
and each q is independently 0-2.

7. A compound of the formula:

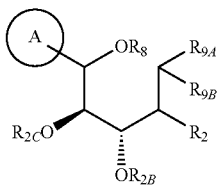

or a pharmaceutically acceptable salt thereof, wherein:
A is optionally substituted aryl, cycloalkyl, or heterocycle;
$R_2$ is fluoro or $OR_{2A}$;
each of $R_{2A}$, $R_{2B}$, and $R_{2C}$ is independently hydrogen, optionally substituted alkyl, C(O)alkyl, C(O)aryl or aryl;
$R_8$ is hydrogen or $C(O)R_{8A}$;
$R_{8A}$ is hydrogen or optionally substituted alkyl, alkoxy or aryl;
$R_{9A}$ and $R_{9B}$ are each independently $OR_{9C}$ or $SR_{9C}$, or are taken together to provide O, S or $NR_{9C}$; and
each $R_{9C}$ is independently optionally substituted alkyl, aryl or heterocycle.

8. A compound of the formula:
or a pharmaceutically acceptable salt thereof, wherein:
A is optionally substituted aryl, cycloalkyl, or heterocycle;
$R_2$ is fluoro or $OR_{2A}$;
each of $R_{2A}$, $R_{2B}$, and $R_{2C}$ is independently hydrogen, optionally substituted alkyl, C(O)alkyl, C(O)aryl or aryl;
$R_3$ is hydrogen or optionally substituted alkyl, aryl or heterocycle;
$R_8$ is hydrogen or $C(O)R_{8A}$;
$R_{8A}$ is hydrogen or optionally substituted alkyl, alkoxy or aryl;
$R_{9A}$ and $R_{9B}$ are each independently $OR_{9C}$ or $SR_{9C}$, or are taken together to provide O, S or $NR_{9C}$; and
each $R_{9C}$ is independently optionally substituted alkyl, aryl or heterocycle.

9. A pharmaceutical formulation comprising a compound of claim 4 and a pharmaceutically acceptable diluent or excipient.

10. A method of inhibiting sodium glucose co-transporter 2 activity, which comprises contacting sodium glucose co-transporter 2 with an effective amount of a compound of claim 4.

11. A method of decreasing blood glucose in a patient, which comprises administering to the patient an effective amount of a compound of claim 4.

12. A method of increasing the excretion of glucose in the urine of a patient, which comprises administering to the patient an effective amount of a compound of claim 4.

13. A method of restoring insulin sensitivity in a patient, which comprises administering to a patient in need thereof an effective amount of a compound of claim 4.

14. A method of treating or managing a disease or disorder in a patient, which comprises administering to a patient in need thereof a therapeutically effective amount of a compound of claim 4, wherein the disease or disorder is atherosclerosis, cardiovascular disease, diabetes (Type 1 or 2), hyperglycemia, hypertension, lipid disorders, obesity, or Syndrome X.

15. The method of claim 14, wherein the disease or disorder is type 2 diabetes.

16. A pharmaceutical formulation comprising a compound of claim 5 and a pharmaceutically acceptable diluent or excipient.

17. A method of inhibiting sodium glucose co-transporter 2 activity, which comprises contacting sodium glucose co-transporter 2 with an effective amount of a compound of claim 5.

18. A method of decreasing blood glucose in a patient, which comprises administering to the patient an effective amount of a compound of claim 5.

19. A method of increasing the excretion of glucose in the urine of a patient, which comprises administering to the patient an effective amount of a compound of claim 5.

20. A method of restoring insulin sensitivity in a patient, which comprises administering to a patient in need thereof an effective amount of a compound of claim 5.

21. A method of treating or managing a disease or disorder in a patient, which comprises administering to a patient in need thereof a therapeutically effective amount of a compound of claim 5, wherein the disease or disorder is atherosclerosis, cardiovascular disease, diabetes (Type 1 or 2), hyperglycemia, hypertension, lipid disorders, obesity, or Syndrome X.

22. The method of claim 21, wherein the disease or disorder is type 2 diabetes.

23. The compound of claim 4, wherein $R_{1A}$ is lower alkyl.

24. The compound of claim 5, wherein $R_{1A}$ is lower alkyl.

25. (2S,3R,4R,5S,6R)-2-[4-chloro-3-(4-ethoxy-benzyl)-phenyl]-6-methylsulfanyl-tetrahydro-pyran-3,4,5-triol or a pharmaceutically acceptable salt thereof.

26. A pharmaceutical formulation comprising (2S,3R,4R,5S,6R)-2-[4-chloro-3-(4-ethoxy-benzyl)-phenyl]-6-methylsulfanyl-tetrahydro-pyran-3,4,5-triol or a pharmaceutically acceptable salt thereof, and a pharmaceutically acceptable diluent or excipient.

27. A method of treating type 2 diabetes in a patient, which comprises administering to a patient in need thereof a therapeutically effective amount of (2S,3R,4R,5S,6R)-2-[4-chloro-3-(4-ethoxy-benzyl)-phenyl]-6-methylsulfanyl-tetrahydro-pyran-3,4,5-triol or a pharmaceutically acceptable salt thereof.

* * * * *

UNITED STATES PATENT AND TRADEMARK OFFICE
CERTIFICATE OF CORRECTION

PATENT NO. : 7,781,577 B2
APPLICATION NO. : 11/862690
DATED : August 24, 2010
INVENTOR(S) : Harrison et al.

It is certified that error appears in the above-identified patent and that said Letters Patent is hereby corrected as shown below:

Title page, item (75), should read as follows:
Bryce Alden Harrison, Hamilton, NJ (US);
Spencer David Kimball, East Windsor, NJ (US);
Ross Mabon, Princeton, NJ (US);
David Brent Rawlins, Morrisville, PA (US)

Claim 1, line 4, "R1" should be changed to --$R_1$--.

Claim 1, line 9, "C{O)aryl" should be changed to --C(O)aryl--.

Claim 6, line 23, "alkyl," should be changed to --alkyl;--.

Claim 8, insert the following formula between lines 1 and 2:

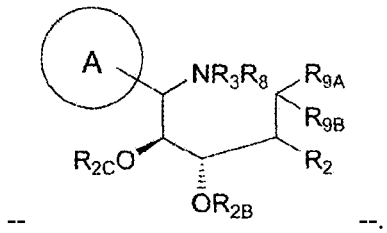

Signed and Sealed this
Thirtieth Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,781,577 B2  
APPLICATION NO. : 11/864690  
DATED : August 24, 2010  
INVENTOR(S) : Harrison et al.

Page 1 of 1

It is certified that error appears in the above-identified patent and that said Letters Patent is hereby corrected as shown below:

Title page, item (75), should read as follows:
Bryce Alden Harrison, Hamilton, NJ (US);
Spencer David Kimball, East Windsor, NJ (US);
Ross Mabon, Princeton, NJ (US);
David Brent Rawlins, Morrisville, PA (US)

Column 47, line 40 (Claim 1, line 4) "R1" should be changed to --$R_1$--.

Column 47, line 45 (Claim 1, line 9) "C{O)aryl" should be changed to --C(O)aryl--.

Column 48, line 64 (Claim 6, line 23) "alkyl," should be changed to --alkyl;--.

Column 49, insert the following formula between lines 26 and 27 (Claim 8, lines 1 and 2):

-- 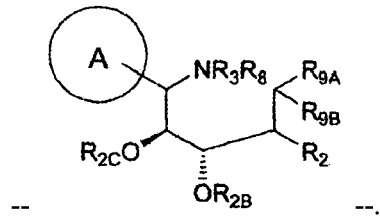 --.

This certificate supersedes the Certificate of Correction issued August 30, 2011.

Signed and Sealed this
Eleventh Day of October, 2011

David J. Kappos
*Director of the United States Patent and Trademark Office*

UNITED STATES PATENT AND TRADEMARK OFFICE

(12)         CERTIFICATE EXTENDING PATENT TERM
                    UNDER 35 U.S.C. 156

| | | | |
|---|---|---|---|
| (68) | PATENT NO. | : | 7,781,577 |
| (45) | ISSUED | : | August 24, 2010 |
| (75) | INVENTOR | : | Bryce Alden HARRISON; Spencer David KIMBALL; Ross MABON; and David Brent RAWLINS |
| (73) | PATENT OWNER | : | Lexicon Pharmaceuticals, Inc. |
| (95) | PRODUCT | : | INPEFA® (sotagliflozin) |

This is to certify that an application under 35 U.S.C. 156 has been filed in the United States Patent and Trademark Office, requesting extension of the term of U.S. Patent No. 7,781,577 based upon the regulatory review of the product INPEFA® (sotagliflozin) by the Food and Drug Administration. According to United States Patent and Trademark Office records, the original expiration date of the patent as of the date of issuance of this certificate is May 4, 2028. Because it appears that the requirements of the law have been met, this certificate extends the term of the patent for the period of

(94)                              five years subject to the payment of maintenance fees as provided by law, with all rights pertaining thereto as provided by 35 U.S.C. 156.

I have caused the seal of the United States Patent and Trademark Office to be affixed this 13th day of November 2025.

John A. Squires
Under Secretary of Commerce for Intellectual Property and
Director of the United States Patent and Trademark Office